[19] United States Patent
Fang et al.

[11] Patent Number: 5,309,907
[45] Date of Patent: May 10, 1994

[54] MEASURING ARRANGEMENT FOR EXAMINING A SUBJECT WITH VISIBLE, NIR OR IR LIGHT

[75] Inventors: Ming Fang, Plainsboro, N.J.; Hans-Erich Reinfelder, Erlangen, Fed. Rep. of Germany

[73] Assignee: Siemens Aktiengesellschaft, Munich, Fed. Rep. of Germany

[21] Appl. No.: 935,878

[22] Filed: Aug. 26, 1992

[30] Foreign Application Priority Data

Sep. 4, 1991 [DE] Fed. Rep. of Germany ....... 4129438

[51] Int. Cl.[5] ............................................... A61B 5/00
[52] U.S. Cl. ................................... 128/633; 128/664; 128/665
[58] Field of Search ............................... 128/633–634, 128/664–665, 666–667

[56] References Cited

U.S. PATENT DOCUMENTS 5,122,974 6/1992 Chance .......................... 128/633 X
5,213,105 5/1993 Gratton et al. ...................... 128/664

FOREIGN PATENT DOCUMENTS 3135070 3/1983 Fed. Rep. of Germany .

OTHER PUBLICATIONS

"Cerebral Oxygenation Measuring System NIR-1000 (Tentative Data)" Hamamatsu Photonics K.K. System Division (Sep. 1987).

"Optical-Spectroscopy," Egan et al., Acta Radiologica, vol. 29, Fasc. 5, Sep.–Oct., 1988.

"Cerebral Monitoring in Newborn Infants by Magnetic Resonance and Near Infrared Spectroscopy," Delpy et al., Departments of Medical Physics and Bioengineering, Pediatrics and Physiology, Iniversity College London.

"Estimation of Optical Pathlength Through Tissue from Direct Time of Flight Measurement," Delpy et al., Phys. Med. Biol., 1988, vol. 33, No. 12, pp. 1433–1442.

"Distance Measurement by the Wavelength Shift of Laser Diode Light," Kikuta et al., Appl. Opt., vol. 25, No. 17, Sep., 1986, pp. 2976–2980.

"Speckle Interferometry," Ennos, in Laser Speckle and Related Phenomena, Dainty, Ed. 1984, pp. 203–253.

Primary Examiner—Angela D. Sykes
Attorney, Agent, or Firm—Hill, Steadman & Simpson

[57] ABSTRACT

An apparatus for examining tissue in vivo by means of the optical properties of the tissue generates a measuring chirp signal which is introduced into a tissue-containing subject as a coherent optical chirp signal. The parts of the measuring chirp signal emerging from the subject are superimposed with a reference chirp signal to form a superposition signal that is supplied to a filter that only allows those parts of the superposition signal to pass that represent those parts of the measuring chirp signal emerging from the subject which have traversed a defined, optical path length within the subject.

80 Claims, 9 Drawing Sheets

MEASURING ARRANGEMENT FOR EXAMINING A SUBJECT WITH VISIBLE, NIR OR IR LIGHT

BACKGROUND OF THE INVENTION

1. Field of the Invention

The present invention is directed to a tissue-optical measuring arrangement for the examination of a preferably living subject with visible, NIR or IR light, i.e. the examination is carried out in vivo preferably. The wavelength of the visible light thereby lies between 380 and 780 nm, that of NIR light (near infrared light) lies between 780 nm and 1.5 μm and that of IR light (infrared light) lies between 1.5 μm and 1 mm, whereby it is particularly the range from 1.5 μm through 15 μm that is of significance in the present invention given the employment of IR light.

2. Description of the Prior Art

Many optical properties of tissue such as, for example, the absorption, the scattering or dispersion and the spectral properties can be identified by directing light of the aforementioned wavelength ranges at a region of the subject. For example, it is possible to identify tissue modifications in mammary diagnostics or to acquire information about the blood supply of the brain in pediatrics and/or neurology by directing light of the aforementioned wavelength ranges, for example at a mammary gland or a skull, with the light emerging from the subject being detected and the information acquired in this way being interpreted by a suitable technique. It is thereby advantageous that these are usually non-invasive procedures. Further details of examination of this type are discussed, can be derived, for example, in the publications "Cerebral Oxygenation Measuring System NIR-100" (Tentative Data), Hamamatsu Photonics K. K., System Division, September 1987; "Optical Spectroscopy", Robert L. Egan et al., Acto Radiologica, Vol. 29, Fasc. 5, September-October 1988; "Cerebral Monitoring in Newborn Infants by Magnetic Resonance and Hear Infrared Spectroscopy", D. T. Delpy et al., Departments of Medical Physics and Bioengineering, Pediatrics and Physiology, University College London. Unfortunately, the light emerging from the subject that is to be detected, which can be back-scattered (diffusely reflected) light or dispersed transmitted light, contains information about the entire region of the subject illuminated with the incoming light. The measurement is thus not location-selective. When detecting the back-scattered light, this means that, in particular, one does not know at what depth the light was reflected, i.e. the distance from the surface of the subject measured parallel to the propagation direction of the incident light. This is especially disturbing when one wishes to examine the optical properties of a subject at a specific depth. One must then simultaneously measure most of the light back-scattered from the surface of the subject and the surface-proximate regions thereof. This leads to a poor signal-to-noise ratio of the measurement and can even lead to unusable results of the measurement beginning at a specific thickness of the subject. For measurements wherein the light transmitted through the subject is detected, the lack of location-selectivity means that the path taken by the light transmitted through the subject cannot be specifically identified. Again, the signal-to-noise ratio deteriorates with increasing thickness of the subject, to the point that the measured results are unusable.

Heretofore, only one method fundamentally suitable for employment in vivo was known which, however, only comes closer to resolving the aforementioned problems with extremely great outlay. This method is described in the article "Estimation of Optical Pathlength through Tissue from Direct Time of Flight Measurement", D. T. Delpy et al., Phys. Med. Biol., 1988, Vol. 33, No. 12, pages 1433–1442 and is based on the time of flight measuring principle using a pulsed laser as a light source and an ultra-fast streak camera as a detector. The pulse duration of the laser is typically less than 1 picosecond. The chronological resolution of the streak camera lies on the order of magnitude of approximately 2 picoseconds. Since the light is back-scattered from the subject to be examined in different depths, penetrates the subject on different paths, the individual parts of the back-scattered or transmitted light have different arrival times at the streak camera. The detected light parts can thus be selected and detected according to arrival time, and thus according to the depth in the subject from which they were back-scattered, or the path which they took through the subject. A time of flight measuring system having an adequate chronological resolution, and thus an adequate topical resolution, however, is expensive.

SUMMARY OF THE INVENTION

It is an object of the present invention to provide a tissue-optical measuring arrangement that is simply and economically constructed which nonetheless provides topically selective measurement data.

This object is achieved in accordance with the principles of the present invention in a tissue-optical measuring arrangement for the preferably in vivo examination of wherein coherent visible, NIR or IR light is directed as a measuring chirp signal at a tissue-containing subject with a part of this measuring chirp signal emerging from the subject after interacting with tissue to be analyzed. A reference chirp signal, having a defined phase relationship to the measuring chirp signal, is also generated. The reference chirp signal is superimposed with that part of the measuring chirp signal emerging from the subject, to form a superposition signal having beats at a beat frequency, due to the out-of-phase relationship between the two signals. This superposition signal is supplied to a filter which has an amplitude-frequency response with a trailing edge above an upper limit frequency. The parameters of the transit time of the measuring chirp signal outside the subject, the transit time of the reference chirp signal, and the upper limit frequency of the filter are dimensioned so that the filtered signal represents substantially only those parts of the signal emerging from the subject which have traversed an optical path length in the subject which does not exceed a defined maximum optical path length.

When phase shifts are present between the reference chirp signal and the chirp signals contained in the measuring chirp signal, the superposed signal contains beat signals that arise due to superimposition of the individual chirp signals contained in the measuring chirp signal, which one chronologically offset relative to the reference chirp signal, with the reference chirp signal. The coherent light chirp signal supplied to the subject as a measurement chirp signal, for example, may have a light frequency changing linearly over time between an upper and lower limit value and the reference chirp signal may have a corresponding signal parameter that likewise changes linearly over time during a signal period between an upper and lower limit value. This results in the frequencies of the individual beat signals being directly proportional to the respective time differences between the chirp signals contained in those parts of the measuring chirp signal emerging from the subject and the reference chirp signal. When the transit time of the measuring chirp signal outside the examination subject (which is the total transit time of the coherent light chirp signal within the subject) and the transit time of the reference chirp signal (which is the transit time thereof from the means for generating a reference chirp signal to the means for superimposition) are known, the optical path length traversed inside the subject by the corresponding part of the measuring chirp signal emerging from the subject can be identified from the respective beat frequencies, or time differences. The output signal of the filter essentially only represents those parts of the measuring chirp signal emerging from the examination subject which were superimposed with the reference chirp signal to form beat signals having beat frequencies at most equal to the upper limit frequency of the filter. Therefore, only those parts of the measuring chirp signal emerging from the examination subject are represented in the output signal of the filter whose optical path length in the subject does not exceed a maximum optical path length in the subject. In addition to being dependent on the transit time of the measuring chirp signal outside the subject under examination and the running time of the reference chirp signal, the filter output signal is also dependent on the upper limit frequency of the filter. For measurements wherein that part of the measuring chirp signal transmitted through the subject under examination is taken into consideration, this means that only those parts of the measuring chirp signal transmitted through the subject are represented in the output signal of the filter whose path in the examination subject proceeds in a cigar-shaped region connecting the light entry zone to the light exit zone. This region has a boundary line of a length that is equal to the maximum optical path length in the subject. For measurements wherein those parts of the measuring chirp signal back-scattered from the examination subject are taken into consideration, by contrast, only those back-scattered parts of the measuring chirp signal emerging from the subject are represented in the output signal of the filter that are back-scattered from a depth of the subject under examination that is at most equal to half the maximum optical path length in the subject. Thus topically resolving tissue-optical measurements are possible with a relatively simple measuring arrangement.

Although it is adequate that the filter has only an upper limit frequency, i.e. has a low-pass characteristic, a preferred version of the invention, which is particularly advantageous when the back-scattered light is detected, has a filter that also has a lower limit frequency. When the upper and lower limit frequencies of the filter lie close to one another or even coincide (band-pass), accordingly, the output signal of the filter only represents that part of the measuring chirp signal back-scattered from the subject that arises from a defined depth of the subject. This defined depth is determined by the transit time of the measuring chirp signal outside the subject and the transit time of the reference chirp signal as well as by the limit frequencies of the filter means. That depth can be varied by varying at least one of the parameters from the group of transit time of the measuring chirp signal outside the subject under examination, transit time of the reference chirp signal, upper/lower limit frequency of the filter.

This embodiment of the invention with upper and lower filter frequency limits is also advantageous in measurements wherein the part of the measuring chirp signal transmitted through the subject is taken into consideration since not only can disturbances be blanked out as a consequence of the lower limit frequency of the filter, but also the diameter of the cigar-shaped region can be varied by varying at least one of the parameters of the aforementioned group of parameters (with the exception of the lower limit frequency). The lower limit frequency of the filter means, however, should be selected low enough so that the part of the measuring chirp signal that takes the direct route through the examination subject is still represented in the output signal of the filter. Moreover, with "knowledge" of the selected values of the aforementioned variable parameters, an evaluation unit can calculate the optical path length traversed in the subject by those parts of the measuring chirp signal represented in the output signal of the filter and emerging from the subject.

Both the measuring chirp signal and the reference chirp signal can be optical chirp signals, whereby those parts of the measuring chirp signal emerging from the subject are optically superimposed with the reference chirp signal and the optical superposition signal thereby arising is supplied to a detector for conversion into an electrical signal supplied to the filter.

It is possible, however, that only the measuring chirp signal is an optical chirp signal, whereas an electrical chirp signal is generated as the reference chirp signal. Those parts of the measuring chirp signal emerging from the subject are then converted into an electrical signal that is superimposed on the electrical reference chirp signal in a mixer stage. The electrical output signal of the mixer stage is supplied to the filter.

In the above embodiments, the measuring chirp signal can be optionally amplitude-modulated in view of the optical intensity or frequency-modulated in view of the optical frequency. In a further embodiment, however, a measuring chirp signal that is amplitude-modulated in view of the optical intensity is required, since the detector used for detecting those parts of the measuring chirp signal emerging from the subject only responds to changes in the optical intensity but not in the optical frequency. The change of the optical frequency over time and/or the change of the frequency of the variation in optical intensity over time preferably ensue linearly both in the embodiments wherein modulation is optional in the embodiment wherein modulation is required. However, only a change which is defined over time is needed (i.e., the defined change need not necessarily vary linearly).

Further embodiments allow a scanning of the examination subject with the measuring chirp signal. In one of these embodiments relative motion between the subject and light exit and entry zones is executed. Light directed at the patient exits from a light source from a light exit zone and light emerging from the subject enters a detector via a light entry zone. In another of these embodiments, a plurality of detectors are used, each having a light entry zone into which some of the light emerging from the subject enters. This embodiment has the advantage that the detector units of the detector means can remain stationary relative to the subject during the scan event. In another of these scanning embodiments, a single light source having multiple light exit zones, or a plurality of light sources, may be used so that mechanical movements of the light exit zones and of the detector units relative to the subject are entirely avoided. The embodiments wherein relative movement is actually executed, or is electronically simulated, allow an at least two-dimensional absorption array of absorption coefficients of the subject under examination to be identified and displayed. Given the use of optical chirp signals having light with different wavelengths, absorption arrays for different wavelengths can also be identified, this being critical for spectroscopic examinations.

DESCRIPTION OF THE PREFERRED EMBODIMENTS

Figure 1:
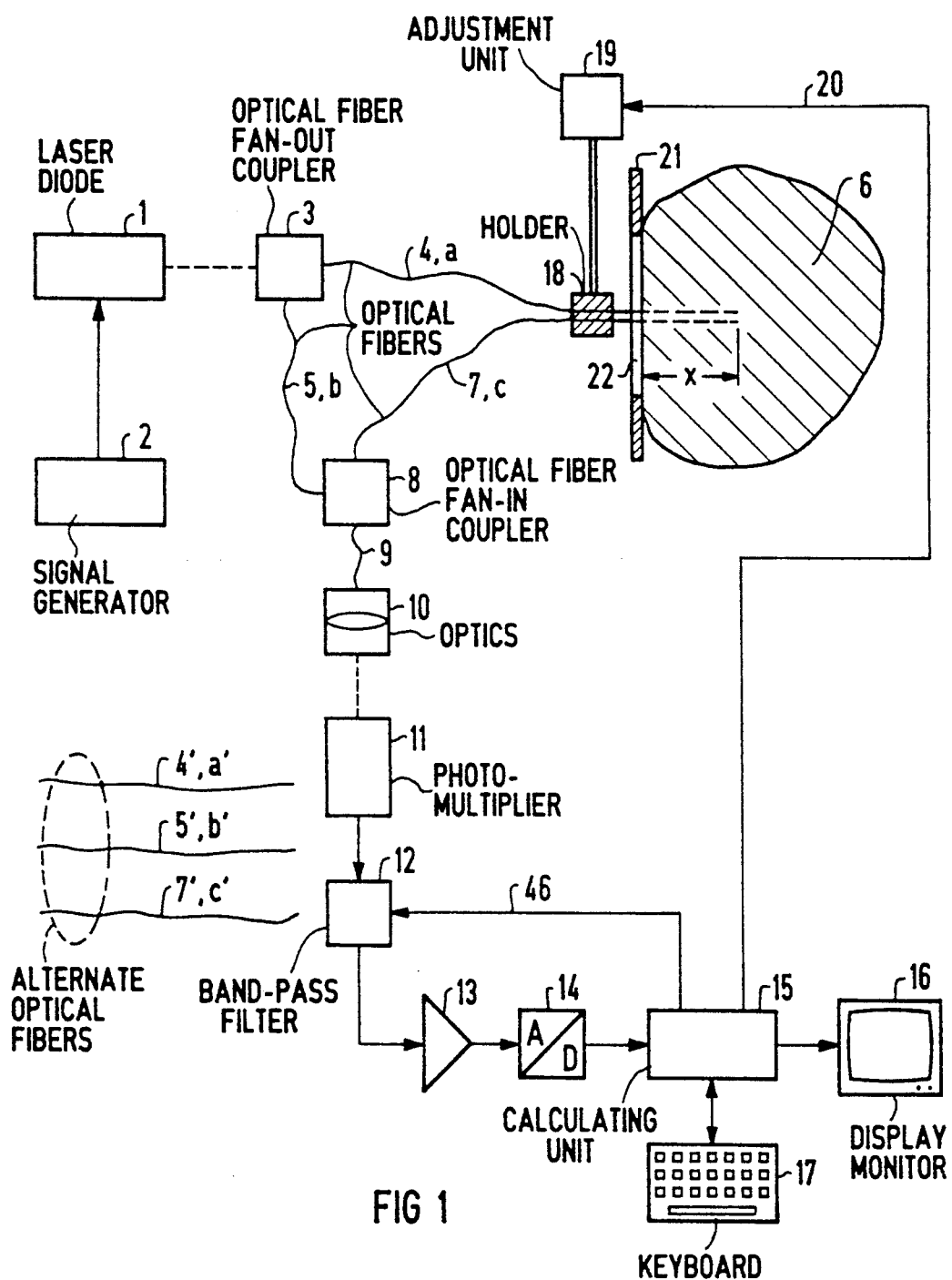
FIG. 1 shows a measuring arrangement constructed in accordance with the principles of the present invention working according to the reflection principle, shown in the form of a block circuit diagram.
Figure 2:
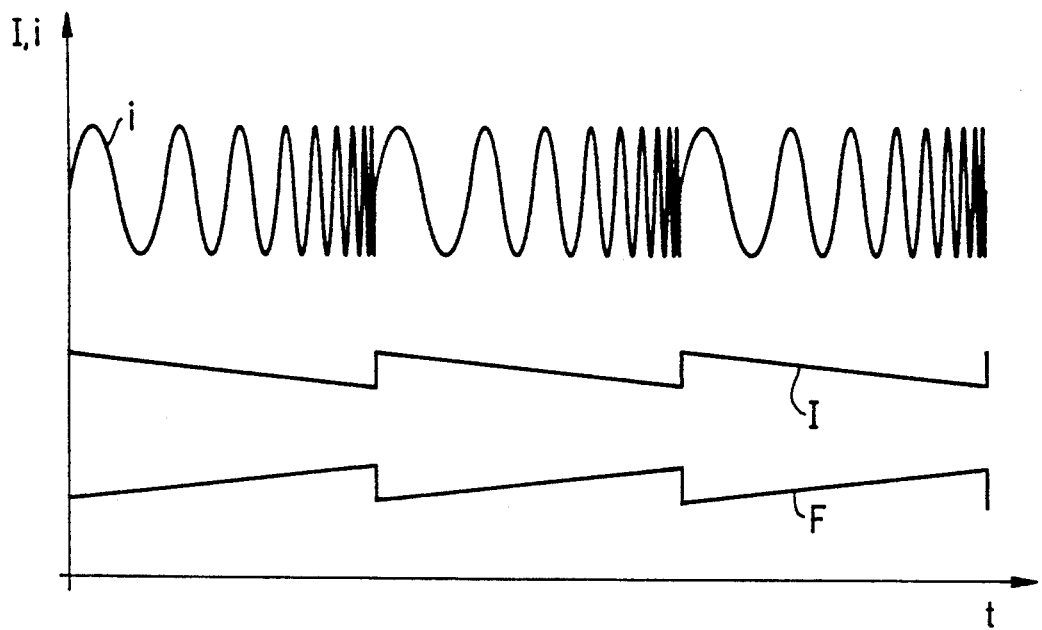
FIG. 2 is a diagram illustrating the chronological curve of the measuring chirp signal and of the reference chirp signal dependent on the operating current of the light source.

The measuring arrangement according to FIG. 1 employs an essentially monochromatic light source which may be, for example, a laser diode 1, which emits coherent light having a wavelength of, for example, 840 nm. The laser diode 1 is in communication with a signal generator 2 that supplies the laser diode 1 with its operating current in the form of an electrical sawtooth signal whose chronological curve is shown in the middle in FIG. 2, whereby FIG. 2 shows the curve of the current intensity I of the sawtooth signal over the time t. The variation of the current intensity of the sawtooth signal per time unit is constant, i.e. the sawtooth signal has a linearly trailing edge. As a consequence of the fact that the frequency of the light emanating from the laser diode 1 is dependent within certain limits on the height of the operating current of the laser diode 1, (it has been found that a variation of the operating current by −1 mA leads to a variation of approximately +2.5 GHz in the frequency of the light emanating from a laser diode, see "Distance measurement by the wavelength shift of laser diode light", H. Kikuta et al., Appl. Opt. Vol. 25, No. 17, September 1986), the laser diode 1 can be frequency-modulated with respect to the frequency of the light it emits. Accordingly, the laser diode 1 generates output in the form of an optical chirp signal that, according to the lower illustration in FIG. 2, has a constant change in the frequency F of the light emitted by the laser diode 1 per time unit, i.e. the optical frequency F linearly varies over the time t between an upper and a lower limit value during a period of the optical chirp signal which corresponds to the period of the electrical sawtooth signal. The chronological curve of the amplitude, i.e. of the intensity i of the optical chirp signal, is qualitatively shown at the top in FIG. 2. It can be seen that the intensity change thereby ensues with the optical frequency. It should be noted that the changing current intensity I of the sawtooth signal also leads to a slight intensity modulation of the light emanating from the laser diode 1 which, however, can be neglected in the context of the invention.

The light emanating from the laser diode 1 proceeds to an optical fiber fan-out coupler 3 that acts as a beam splitter, and one part of the optical chirp signal is coupled into a flexible optical fiber 4, having the length "a" as the measuring chirp signal, referred to below as the measuring light signal. Another part of the optical chirp signal is coupled into an optical fiber 5, having the length "b", as the reference chirp signal, referred to below as the reference light signal. The measuring light signal corresponding to the optical chirp signal generated by the laser diode 1, apart from its lower amplitude, is supplied via the optical fiber 4 to an examination subject 6, for example a female breast. The measuring light signal partly penetrates into the subject 6. The part of the measuring light signal back-scattered from the subject 6 proceeds via a flexible optical fiber 7, having the length "c", to an optical fiber fan-in coupler 8, to which the optical fiber 5 is also connected. The optical fiber fan-in coupler 8 thus superimposes the reference light signal with those parts of the measuring light signal emerging from the subject 6 to from a superposition signal. The superimposition light signal proceeds via an optical fiber 9 to an optics 10 and then to a detector, for example, a photomultiplier 11. The electrical signal available at the output of the photomultiplier 11 thus represents the superposition light signal or, stated more precisely, represents the chronical curve of its intensity. This electrical signal proceeds to a band-pass filter 12 which, as shown in FIG. 1, is followed by an amplifier 13 as warranted. The amplified output signal of the band-pass filter 12 proceeds to an analog-to-digital converter 14 whose digital output data are supplied to an electronic calculating unit 15 to which a monitor 16 and a keyboard 17 are connected.

The optical fibers 4 and 7 are accepted in a holder 18 so that their ends are situated in close proximity to one another and, preferably, close to the surface of the subject 6, whereby the end of the optical fiber 4 represents the light exit zone and the end of the optical fiber 7 represents the light entry zone of the measuring arrangement. The center axes of the ends of the optical fibers 4 and 7 accepted in the holder 18 proceed substantially parallel. The holder 18 is connected to an adjustment unit 19, which is actuatable with the electronic calculating unit 15 via a control line 20, for displacing the holder 18 relative to the subject 6. The electronic calculating unit 15 is also able to adjust the center frequency of the band-pass filter 12 via a control line 46.

Optical fibers 4', 5' and 7', which are respectively interchangeable individually or in groups with optical fibers 4, 5 and 7 are provided to vary the transit times of the reference light signal from the optical fiber fan-out coupler 3 to the optical fiber fan-in coupler 8 and the transit time of the measuring light outside the subject 6. This latter transit time is the transit time of the measuring light signal from the optical fiber fan-out coupler 3 through the optical fiber 4 to the surface of the subject 6 and the transit time of those parts of the measuring light signal back-scattered from the subject 6 from the surface of the subject 6 through the optical fiber 7 to the optical fiber fan-in coupler 8. Since the aforementioned transit times are dependent on the lengths of the traversed optical fibers and on the refractive indices of their materials, the optical fibers 4', 5', 7' differ from the corresponding optical fibers 4, 5, 7 in view of their respective lengths a', b', c' and/or in view of the refractive indices of their materials, so that respectively different transit times occur.

When the measuring light signal is introduced into the subject 6, it is scattered or dispersed as a consequence of the fact that the breast tissue, like all tissue is an opaque medium. This results in a part of the measuring light signal being back-scattered and proceeding through the optical fiber 7 to the optical fiber fan-in coupler 8. As a consequence of the fact that the optical chirp signal introduced into the subject 6 as the measuring light signal is back-scattered from points of the subject 6 that are at different distances from the light exit and light entry zone, this back-scattered light represents a mixture of optical chirp signals of different amplitudes that are chronologically offset vis-a-vis one another. Each optical chirp signal represents a back-scattered part of the measuring light signal introduced into the subject 6. The size of the amplitudes of the optical chirp signals contained in the mix depends, first, on the optical path lengths which the individual optical chirp signals of the mix traversed in the subject 6 and, second, on the absorption properties of the regions of the subject 6 traversed by the individual optical chirp signals. This mix of back-scattered optical chirp signals and the reference light signal are superimposed with the optical fiber fan-in coupler 8 to form the superposition light signal. Since both the reference light signal and the optical chirp signals contained in the parts of the measuring light signal back-scattered from the subject 4 have a change in optical frequency that is constant per time unit, the superposition light signal is a mix of optical signals with sets of beats at respective beat frequencies in a direct relationship with the respective optical path length traversed in the subject 6 by the optical chirp signals back-scattered from the subject 6. The frequency responses or degrees of modulation of the individual optical beat signals have a direct relationship to the amplitudes of the back-scattered optical chirp signals respectively represented by those signals. The optical beat signals contained in the superposed light signal thus represent the back-scattered parts of the measuring light signal introduced into the subject 6 according to their optical path length traversed in the subject 6 and according to their optical intensity.

Since the amplitudes of the optical chirp signals back-scattered from the subject 6 are substantially lower than those of the reference light signal, it can be expedient for improving the signal quality to attenuate the reference light signal before it is superimposed with the back-scattered parts of the measuring light signal, because an enhanced frequency response of the optical beat signals can then be achieved. The subjective speckle size arising as a result of the above-described superimposition (in this respect, see "Speckle Interferometry", A. E. Ennos in Laser Speckle and Related Phenomena, Edited by I. C. Dainty, Springer-Verlag, 1984) is magnified to such an extent by the optics 10 that it is adequate for detection with the photomultiplier 11. The output signal of the photomultiplier 11 is a mix of electrical beat signals corresponding to the optical beat signals contained in the superposition light signal which proceeds to the band-pass filter 12. When the center frequency thereof suitably selected, taking both the transit time of the reference light signal and the transit time of the measuring light signal outside the subject 6 into consideration (and leaving the finite edge steepness of the band-pass filter 11 out of consideration), the output signal of the band-pass filter 11 contains only beat signals having a beat frequency that corresponds to a specific optical path length of the part of the measuring light signal represented in the beat signal. This is, for example, twice the dimension x (FIG. 1) in the subject 6. It can thus be assumed that the part of the measuring light signal represented in the beat signal filtered out with the band-pass filter 12 was back-scattered from the subject 6 approximately in the depth x.

It is evident that the optical chirp signals contained in that part of the measuring light signal back-scattered from the subject also superimpose with one another to form optical beat signals. In order to be able to separate these beat signals from those beat light signals that arise due to superimposition of the reference light signal with the optical chirp signals contained in that part of the measuring light signal back-scattered from the subject, the transit time of the measuring light signal outside the subject 6 must be greater by a given amount than the transit time of the reference light signal from the optical fiber fan-out coupler 3 to the optical fiber fan-in coupler 8. This given amount, in turn, must be greater than the transit time of that part of the measuring light signal which is still detectable and which was back-scattered from the subject 6 which traversed the longest possible optical path length in the subject 6. Appropriate conditions can be easily set by selecting those optical fibers that yield the required difference in transit time from the optical fibers 4, 4', 5, 5', 7, and 7'. In general, it is adequate when three times the maximum thickness of the subject 6 is assumed as the longest possible optical path length.

Figure 3:
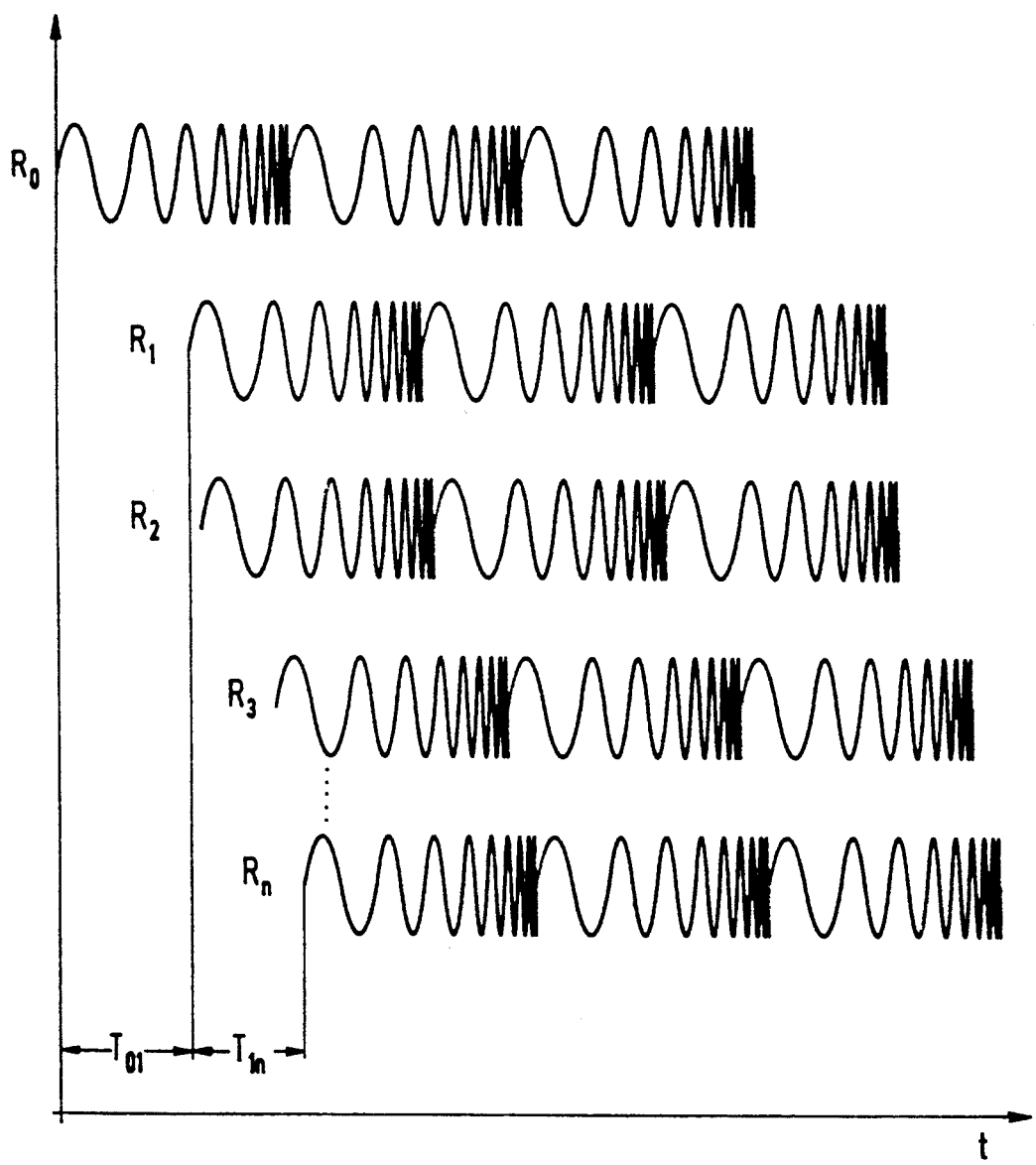
FIG. 3 is a diagram serving for explaining the function of the measuring arrangement according to FIG. 1 which shows the chronological allocation of various parts of the measuring chirp signal emerging from the subject under examination relative to the reference chirp signal.

The above situation is schematically illustrated in FIG. 3 wherein $R_O$ represents the reference light signal, whereas the signals $R_1$ through $R_n$ represent the optical chirp signals contained in that part of the measuring light signal back-scattered from the subject 6 that have traversed optical path lengths of different lengths in the subject 6. The signal $R_1$ thereby represents a part of the measuring light signal reflected immediately at the surface of the subject 4, whereas the signal $R_n$ represents that part of the measuring light signal that traversed the longest possible optical path length in the subject 4. The optical beat signals that arise due to superimposition of the signals $R_1$ through $R_n$ with the reference light signal $R_O$ can then be distinguished from the optical beat signals arising due to superimposition of the signals $R_1$ through $R_n$ with one another when the difference in transit time between the reference light signal $R_O$ and the signal $R_1$—which is referenced $T_{01}$ in FIG. 3—is greater than the transit time difference between the signals $R_1$ and $R_n$ which is referenced $T_{1n}$. The amplitudes of the signals shown in FIG. 3, moreover, are shown equal in size only for simplicity. In practice, the amplitudes of the signals $R_1$ through $R_n$ will differ from one another and will be clearly lower than the amplitude of the reference light signal $R_O$.

Mis-measurements could arise if differences in transit time that exceed a period of the optical chirp signal appear between the reference light signal and an optical chirp signal representing a back-scattered part of the measuring light signal. Such mis-measurements are avoided when the modulation frequency of the optical chirp signal does not significantly exceed 100 MHz. If one assumes a refractive index of $n=1.4$ for tissue, then a back-scattered part of the measuring light signal that has traversed an optical path length of more than 2 m would have to be detected, this being extremely improbable.

Frequencies between 0.1 and 100 MHz are recommended as modulation frequency, i.e. as repetition rate of the measuring chirp signal and, thus, of the optical chirp signal. The center frequency of the sweep of the optical chirp signal corresponds to the optical frequency of the light emanating from the laser diode 1. When the product of modulation frequency and center frequency is greater than $10^{12}$ $Hz^2$ and the sweep is less than 0.5% of the center frequency, topical resolutions on the order of magnitude of 1 mm can be achieved. Consequently, the center frequency must exceed 1 MHz for a required topical resolution of 1 mm and a modulation frequency of 1 MHz, this being guaranteed if one assumes that the wavelength range of infrared light is downwardly limited by 1 mm, corresponding to an optical frequency of 300 GHz. When, as initially specified, a laser diode 1 having a light wavelength of 840 nm is employed, sweep, the variation of the light frequency of the light generated with the laser diode 1, can amount at most to 1.8 THz. In the case of the described exemplary embodiment, the light frequency of the light emanating from the laser diode 1 varies, for example, by 1.0 THz and the frequency change ensues linearly over time.

As may be seen from FIG. 1, the subject 6 lies against a planar plate 21 that is provided with a narrow, straight-line slot 22 wherein the light exit zone of the optical fiber 4 and the light entry zone of the optical fiber 7 are situated. As a consequence of the fact that it is pressed against the stationary plate 21, the surface of the subject 6 is essentially planar. The holder 18 can be adjusted along a straight line with the adjustment unit 19 in the longitudinal direction of the slot 22 and parallel to the plate 21 such that the respective light exit zone or light entry zone of the optical fibers 4 or 7 can be shifted from the one end to the other end of the slot 22 in steps for the purpose of a linear scan motion.

Since the center frequency of the band-pass filter 12 can be adjusted with the electronic calculating unit 15, it is possible to identify a two-dimensional absorption array for the wavelength of the light output by the laser diode 1 with the apparatus of FIG. 1 under the control of an appropriately programmed, electronic calculating unit 15. In such an array, the absorption coefficients for the individual volume elements of a planar slice proceeding through the subject 6 are reproduced in a form corresponding to the geometrical arrangement of the volume elements.

For generating such an array, the electronic calculating unit 15, taking the lengths of the respectively utilized optical fibers 4 or 4', 5 or 5', 7 or 7' into consideration, sets the center frequency of the band-pass filter 12 such that only those optical beat signals that represent back-scattered parts of the measuring light signal that have traversed an optical path length of, for example, 2 mm in the subject 6 can pass the band-pass filter 12. The electronic calculating unit 15 now adjusts the holder 18 step-by-step with a stepping distance of, for example, 1 mm along a path extending on a straight line between a defined starting point and ending point, the length of this path being at most equal to that of the slot 22. From the digital output data of the analog-to-digital converter 13, the electronic calculating unit 15 identifies the optical intensity of the back-scattered part of the measuring light signal respectively represented in the output signal of the band-pass filter 12 for every step of the holder 18 and stores this value. When the holder 18 has arrived at the end point of its path, the electronic calculating unit 15 adjusts the center frequency of the band-pass filter 12 such that only those back-scattered parts of the measuring light signal that have traversed an optical path length of 4 mm in the subject 6 are represented in the output signal of the band-pass filter 12. The electronic calculating unit 15 now causes the holder 18 to again execute its described scan motion and stores the data thereby arising. The described operations—varying the center frequency of the band-pass filter 12 for the purpose of a step-by-step lengthening of the optical path length of the back-scattered parts of the measuring light signal represented in the output signal of the band-pass filter 12 by 2 mm, as well as the implementation of the scan motion and the storing of the data thereby arising—are repeated until a slice having the desired size has been scanned.

According to procedures that are known from x-ray and ultrasound computer tomography, the appropriately programmed electronic calculating unit 15 then calculates the absorption coefficients of the volume elements belonging to the scanned slice from the data registered when scanning the slice. These are relative absorption coefficients which, however, can be converted into absolute absorption coefficients after calibration of the measuring arrangement with a phantom having known absorption properties. The absolute or relative absorption coefficients obtained in this way are numerically displayed by the electronic calculating unit 15 on the monitor 16 in the form of an absorption array. However, there is also the possibility of allocating different grayscale or chromatic values to the different absorption coefficients and displaying these in a graphic illustration on the monitor 16.

Figure 4:
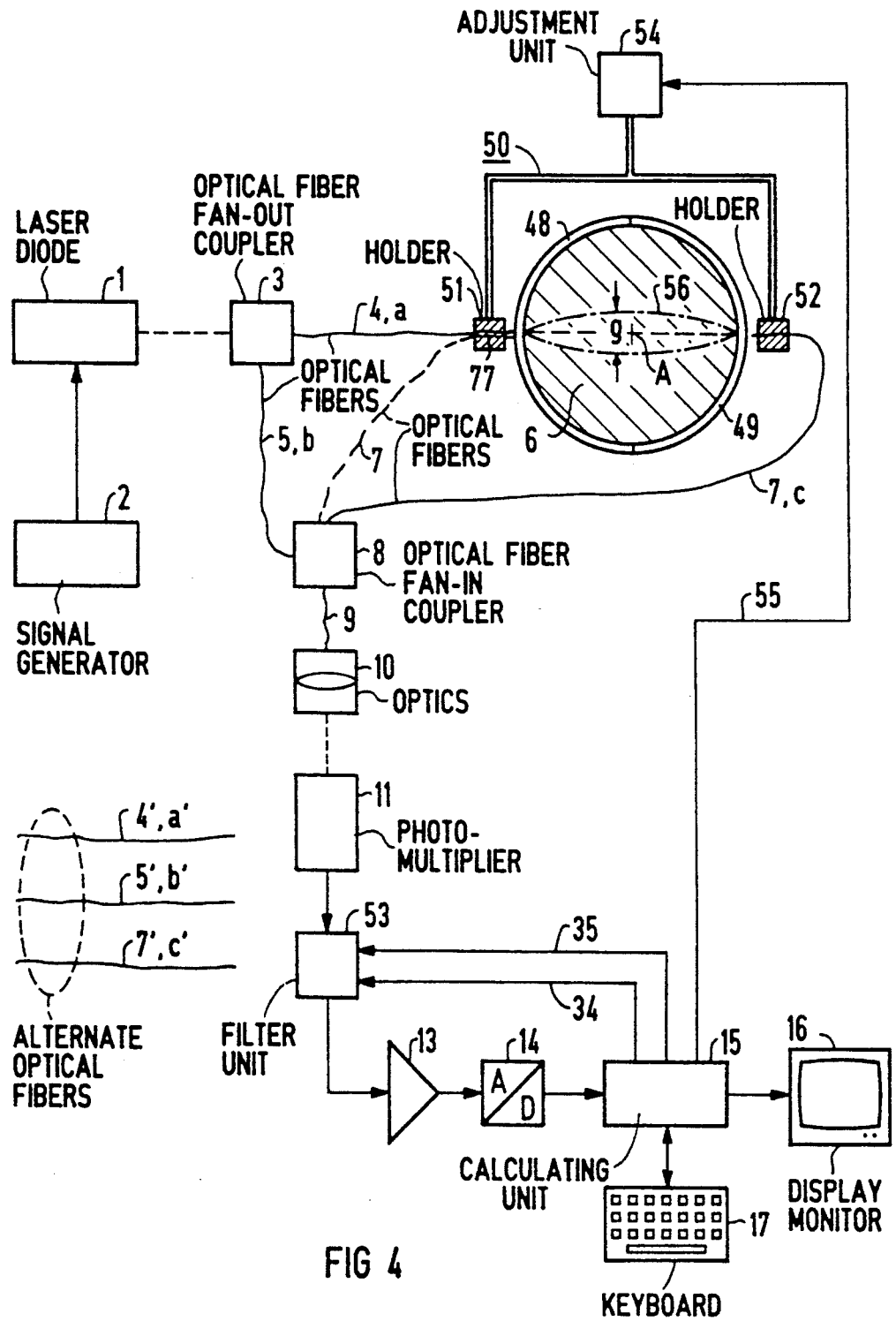
FIG. 4 is a block circuit diagram of a measuring arrangement of the invention preferably operated according to the transmission principle.

The measuring arrangement shown in FIG. 4 largely coincides with that set forth above, for which reason identical elements respectively bear the same reference characters. The essential difference compared to the measuring arrangement set forth above is that it is not the light back-scattered from the subject 6, but the light transmitted through the subject 6 that is detected. To that end, that part of the light transmitted through the subject 6 which emerges from the subject 6 in the region of the light entry zone of the optical fiber 7 is received with the optical fiber 7, whose light entry zone is arranged lying opposite the light exit zone of the optical fiber 4 and is supplied to the optical fiber fan-in coupler 8. The subject 6, which is again a female breast, is accepted between two semicircular shells 48 and 49, that are formed of a material that is highly transparent for the light generated with the laser diode 1. The shells 48 and 49 which have the same radius of curvature and tubularly surround the subject 6, are stationary during the examination. The light exit zone of the optical fiber 4 and the light entry zone of the optical fiber 7 are respectively arranged in close proximity to the shells 48 and 49. The optical fibers 4 and 7 are accepted in alignment with one another in holders 51 and 52 attached in a mount generally referenced 50, such that the center axes of the sections of the optical fibers 4 and 7 accepted in the holders 51 and 52 coincide. As needed, the mount 50 can be rotated step-by-step with the adjustment unit 19, that is in communication with the electronic calculating unit 15 via the control line 20, by at least 180° around an axis A residing at a right angle relative to the plane of the drawing. The axis A coincides with the center axes of the shells 48 and 49 and intersects the center axes of the sections of the optical fibers 4 and 7 accepted in the holders 51 and 52. This rotation is undertaken for the purpose of a scan motion relative to the subject 6 pressed between the shells 48 and 49.

A filter unit 53 is provided instead of the band-pass filter 12 of the measuring arrangement set forth previously. The amplitude-frequency response thereof has a trailing edge below a limit frequency and above an upper limit frequency. The filter unit 53 thus contains a low-pass filter and a high-pass filter that are connected following one another. Both the upper limit frequency as well as the lower limit frequency of the filter unit 53 can be adjusted as needed with the electronic calculating unit 15 via control lines 34 and 35.

Those comments made in conjunction with the measuring arrangement according to FIG. 1 apply analogously with respect to the operation of the measuring arrangement according to FIG. 4, with the difference that a mix of optical chirp signals chronologically offset relative to one another are supplied to the optical fiber fan-in coupler with the optical fiber 7. This mix represents those parts of the measuring light signal supplied to the subject 6 via the optical fiber 4 that are transmitted through the subject 6. Consequently, a superposition optical signal proceeds from the optical fiber fan-in coupler 8 via the optical fiber 9 to the optics 10 and proceeds from the latter to the photomultiplier 11. This superposition light signal is formed by a mix of optical beat light signals, whereby the beat frequencies directly correspond to the optical path lengths and the degrees of modulation directly correspond to the amplitudes of the corresponding parts of the measuring light signal transmitted through the subject 6.

Based on the transit time of the reference light signal through the optical fiber 5, that is established by the length b thereof, and the refractive index of the optical fiber material of the optical fiber 5, and the transit time of the measuring light signal outside the subject 6 (this transit time corresponding to the sum of the transit times of the measuring light signal through the optical fibers 4 and 7 that are again dependent on the lengths a, c of the optical fibers 4, 7 and on the refractive indices of their materials), the lower limit frequency of the filter unit 53 is selected such that optical beat signals that represent those parts of the measuring light signal that have taken the direct path (shown with broken lines in FIG. 4) through the subject 6 have a beat frequency that is at least equal to the lower limit frequency. This is the prerequisite for the electrical beat signals that directly represent parts of the measuring light signal transmitted through the subject 6 passing through the filter unit 53. The maximum optical path length that the parts of the measuring light signal represented in the optical beat signals and transmitted through the subject 6 can have traversed in the subject 6 is defined by the upper limit frequency of the filter unit 53, so that the electrical beat signals representing these parts of the measuring light signal can still pass the filter unit 53. Expressed in other words, thus, only those electrical beat signals can pass the filter unit 53 which represent parts of the measuring light signal transmitted through the subject 6 whose running distance proceeds within the cigar-shaped region 56 shown with dot-dashed lines in FIG. 4, whereby the length of the generated boundary line of the cigar-shaped region 56 corresponds to the maximum optical path length in the subject 6 defined by the upper limit frequency of the filter unit 53. In general, it is adequate when, for example, 1.5 times the maximum thickness of the subject 6 is assumed as the longest possible optical path length of the light within the subject 6. The diameter g of the cigar-shaped region 56 can thus be varied by varying the upper limit frequency of the filter unit 53, whereby the diameter g becomes smaller as the upper limit frequency approaches the lower limit frequency of the filter unit 53. When the upper and lower limit frequencies coincide (band-pass characteristic), only those electrical beat signals can pass through the filter unit 53 which represent parts of the measuring light signal transmitted through the subject 6 that have taken a path through the subject 6 whose length is defined by the common value of the upper and lower limit frequency.

In a manner analogous to FIG. 1, a slice of the subject 6 can also be scanned with the measuring arrangement of FIG. 4, whereby the mount 50 is rotated in steps around the axis A with the adjustment unit 54 and the acquired data proceed to the electronic calculating unit 15 that is suitably programmed in order to calculate and numerically or graphically display a two-dimensional absorption array from the data acquired during the scan event. In order to be able to influence the transit times of the reference light signal to the optical fiber fan-in coupler 8 and/or the transit time of the measuring light signal outside the subject 6, additional optical fibers 4', 5', 7' having lengths a', b', c' and/or refractive indices deviating from those of the optical fibers 4, 5, 7 are provided as set forth above in conjunction with FIG. 1. It is not absolutely necessary that the filter unit 53 also have a lower limit frequency; however, it is advantageous when such a lower limit frequency is present, since noise signals caused, for example, by stray light, can be effectively suppressed.

The measuring arrangement according to FIG. 4 can also be operated in a reflection mode when the optical fiber 7 (as indicated with broken lines in FIG. 4) is introduced into a bore 77 (indicated with broken lines) that proceeds parallel to the bore of the holder 51 that accepts the optical fiber 4. The electronic calculating unit then controls the filter unit 53 via the control lines 34 and 35 such that the upper and the lower limit frequency of the filter unit 53 coincide, i.e. such that a band-pass characteristic is obtained. By gradually varying the center frequency of the set band-pass characteristic for the purpose of elevating the center frequency, annular section planes of the subject 6 can be scanned, their respective diameters becoming smaller with increasing center frequency. With reference to the data identified in this way, the calculating unit 15 is able to calculate and numerically or graphically display a two-dimensional absorption array acquired in the reflection mode.

Figure 5:
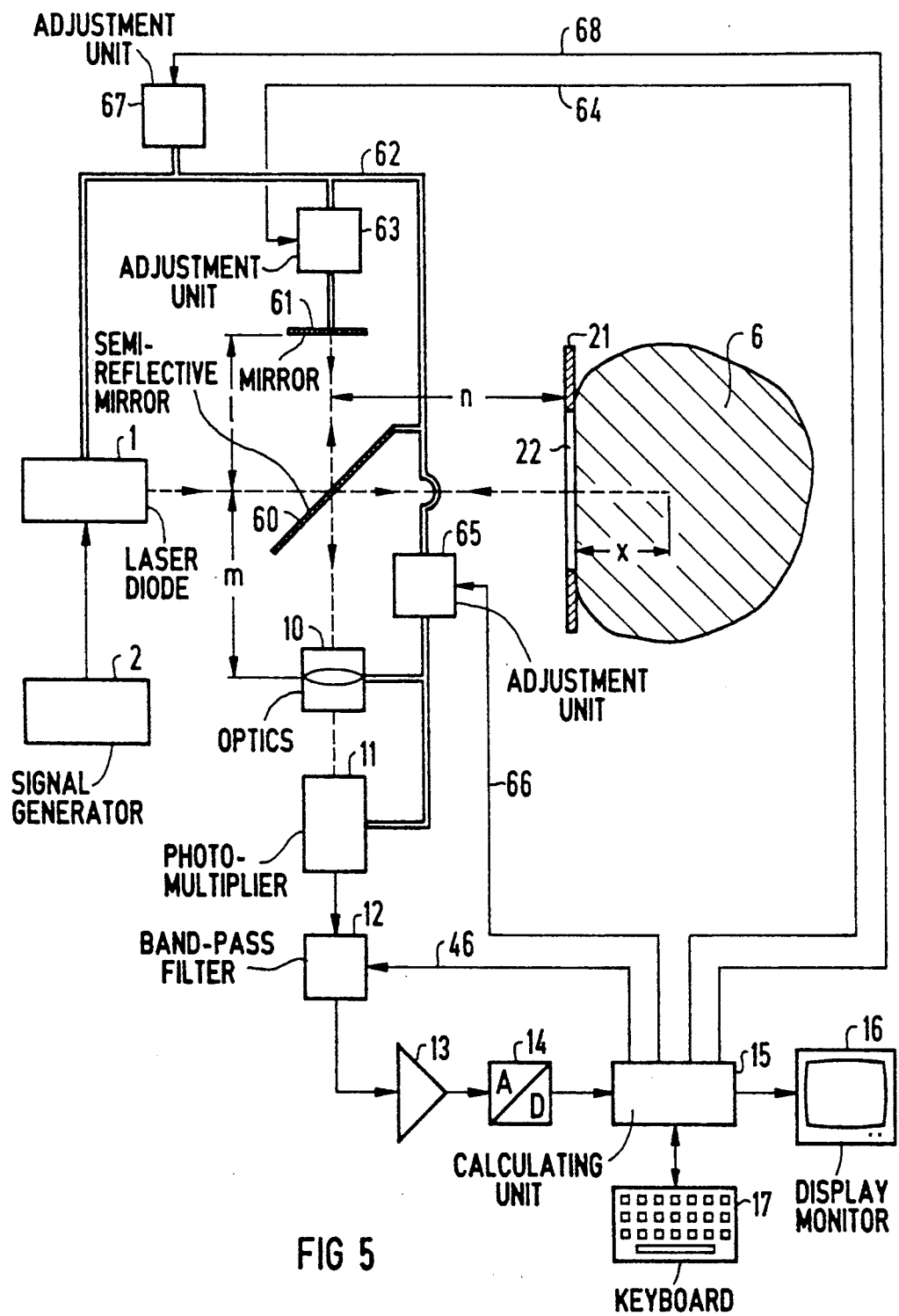
FIG. 5 is a block circuit diagram of a further embodiment of a measuring arrangement of the invention operating according to the reflection principle.

The measuring arrangement of FIG. 5 also coincides with the above-described measuring arrangements, particularly the measuring arrangement of FIG. 1 in terms of certain points, for which reason identical elements bear the same reference characters. A first significant difference in the measuring arrangement of FIG. 5 compared to the measuring arrangement of FIG. 1 is that the functions of the optical fiber fan-out coupler 3 and the optical fiber fan-in coupler 8 are assumed by a single, partially reflective mirror 60. The preferably semi-reflective mirror 60 is arranged relative to the laser diode 1 such that the light emanating therefrom is incident on the mirror 60 at an angle deviating from 90°, preferably at an angle of 45°. The optical chirp signal supplied to the semi-reflective mirror 60 is thus split into a measuring light signal and a reference light signal, whereby the measuring light signal supplied to the subject 6 under examination which, for example, is again a matter of a female breast, is that part of the optical chirp signal that has passed through the semi-reflective mirror 60 and the reference light signal is that part of the optical chirp signal reflected by the semi-reflective mirror 60. The measuring light signal reaching the subject 6 under examination partially penetrates thereinto. The part of the measuring light signal back-scattered from the subject 6 under examination proceeds to the semi-reflective mirror 60 and a part of this back-scattered light of the measuring light signal is reflected by the mirror 60 such that it proceeds through the optics 10 to the photomultiplier 11. The reference light signal proceeds from the semi-reflective mirror 60 to an ordinary mirror 61 that is arranged such that the reference light signal is reflected directly back to the semi-reflective mirror 60. That part of the reference light signal passing through the semi-reflective mirror 60 likewise proceeds through the optics 10 to the photomultiplier 11 and is thereby superimposed on that part of the measuring light signal back-scattered from the object 6 which was reflected at the semi-reflective mirror 60 to form the superposition light signal. That zone of the semi-reflective mirror 60 through which that part of the optical chirp signal supplied to the subject 6 as measuring light signal passes or through which that part of the measuring light signal back-scattered from the subject 6 is incident, represents the light exit zone and simultaneously represents the light entry zone of the measuring arrangement.

The laser diode 1, the optics 10, the photomultiplier 11, the semi-reflective mirror 60 and the mirror 61 are attached to a common frame 62. An adjustment unit 63 for the mirror 61 is provided, actuatable with the electronic calculating unit 15 via a control line 64 for adjusting the spacing l of the mirror 61 from the semi-reflective mirror 60. Moreover, an adjustment unit 65 is provided with which the electronic calculating unit 15 via a control line 66, can adjust the spacing m of the optics 10 from the semi-reflective mirror 60, whereby the spacing of the optics 10 from the photomultiplier 11 is preserved. Finally, an adjustment unit 67 is provided with which the electronic calculating unit 15, via a control line 68, can vary the spacing n of the semi-reflective mirror 60 from the surface of the subject 6 by adjusting the entire frame 62 parallel to the propagation direction of the measuring light signal. By varying the spacings l, m, n, there is the possibility of adapting the measuring arrangement to the respective, specific requirements of an examination case—similar to the interchange of the optical fibers in the case of the measuring arrangements of FIGS. 1 and 4. By varying the spacings l and m, the transit time of the reference light signal from the semi-reflective mirror 60 to the mirror 61 and from the latter back to the semi-reflective mirror 60 can be varied, and the transit time of the measuring light signal outside the subject 6 under examination can be varied by varying the spacings m and n. This latter transit time of the measuring light signal outside the subject 6 under examination is the sum of the transit times of the measuring light signal from the semi-reflective mirror 60 to the surface of the subject 6 and of the back-scattered part of the measuring light signal from the surface of the subject 6 back to the semi-reflective mirror 60.

As may be seen from FIG. 5, the subject 6 again lies against a planar plate 21 that is provided with a narrow, straight line slot 23 through which the measuring light signal enters into the subject 6 and through which that part of the measuring light signal back-scattered from the subject 6 proceeds to the semi-reflective mirror 60 and from the latter through the optics 10 to the photomultiplier 11. In addition to being able to adjust the spacing n, the adjustment unit 67 is fashioned so as also to be able to adjust the frame 62 together with the elements attached thereto in a direction parallel to the longitudinal direction of the slot 22, while retaining the spacings m, l and n. As needed, the electronic calculating unit 15 actuates the adjustment unit 67 via the control line 68 such that the light exit and light entry zone of the measuring arrangement, and thus that zone wherein the measuring light signal enters into the subject 6 and the back-scattered part of the measuring light signal proceeding to the semi-reflective mirror 60 emerges from the subject 6, is displaced step-by-step in the longitudinal direction of the slot 22, and within the slot 22, for the purpose of a linear scan motion. As needed, the electronic calculating unit 15 is also able to adjust the center frequency of the band-pass filter 12 and/or at least one of the spacings l, m, n via the control line 46. With the apparatus according to FIG. 5 under the control of the appropriately programmed, electronic calculating unit 15, it is thus possible to identify a two-dimensional absorption array for the wavelength of the light output by the laser diode 1—similar to that set forth in conjunction with FIG. 1—, whereby the depth x from which the parts of the measuring light signal represented by the output signal of the band-pass filter 12 were back-scattered can be varied by adjusting the aforementioned parameters.

Figure 6:
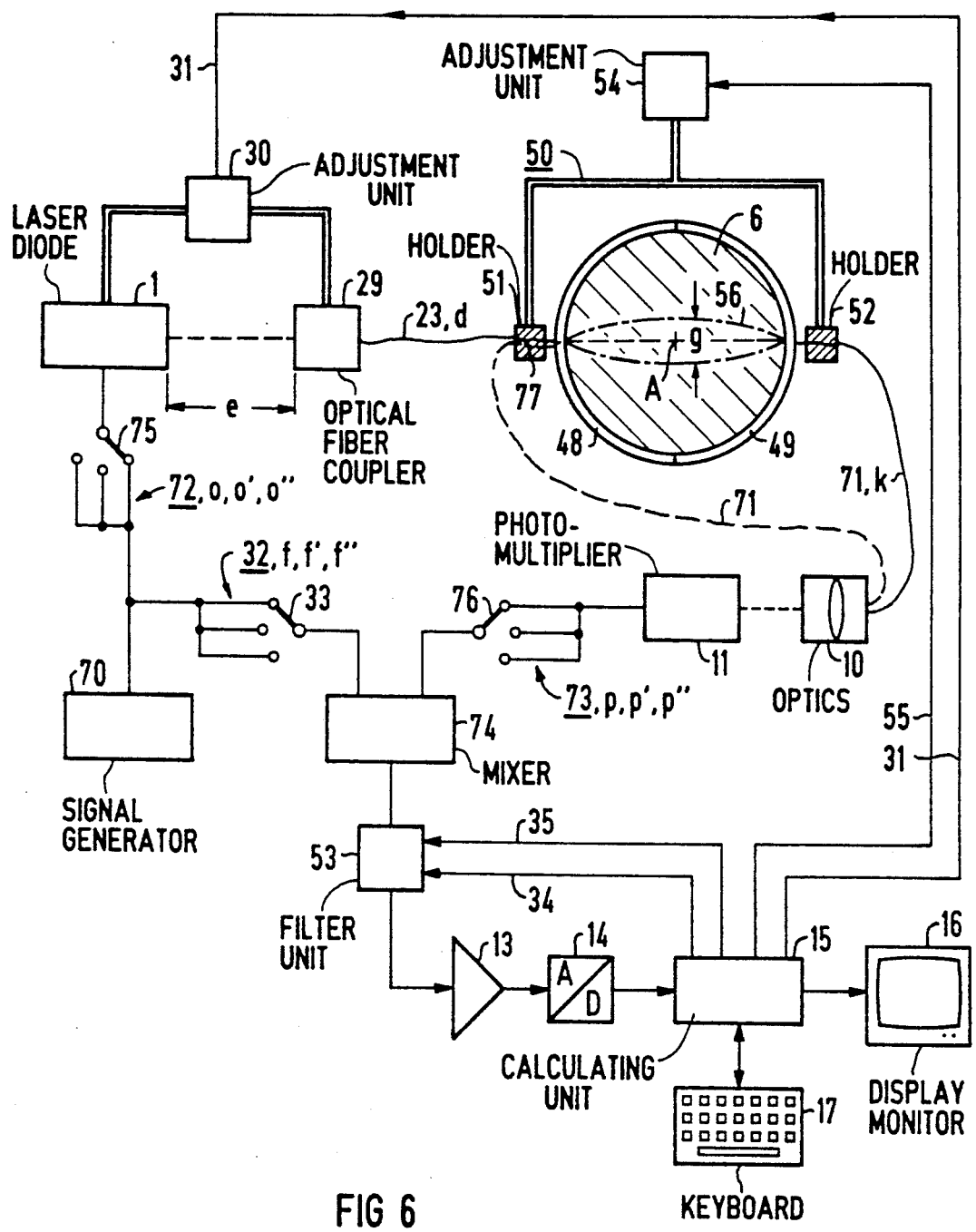
FIG. 6 is a block circuit diagram of another measuring arrangement of the invention preferably operated according to the transmission principle.

The measuring arrangement shown in FIG. 6 agrees with that of FIG. 4 in terms of certain points, for which reason respectively identical elements bear the same reference characters.

Figure 7:
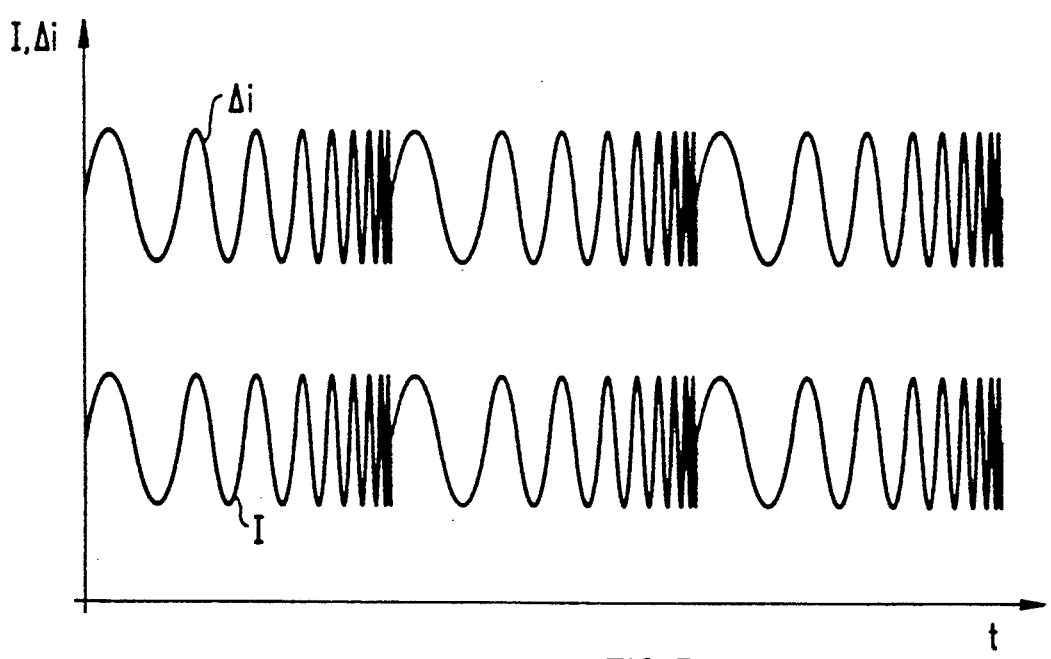
FIG. 7 is a diagram illustrating the chronological curve of the optical chirp signal dependent on the strength of the current of an electrical chirp signal supplied to the light source.

The measuring chirp signal supplied to the subject 6 in the embodiment of FIG. 6 as the measuring light signal is again generated with a laser diode 1 as the light source. By contrast to the exemplary embodiments set forth above, however, this is driven with an electrical chirp signal from a signal generator 70. The curve of the current intensity I of the electrical chirp signal is shown over the time t at the bottom in FIG. 7. During a period of the electrical chirp signal, the frequency of the current changes linearly over the time t between an upper and a lower limit value. As a consequence of the fact that the intensity of the light emanating from the laser diode 1 is proportional to the operating currents applied to the laser diode 1, the laser diode 1 can be amplitude-modulated with respect to the intensity i of the light it emits. When driven with the described, electrical chirp signal, consequently, the laser diode 1 outputs an optical chirp signal that has an intensity change Δi of the light whose curve, according to the upper illustration in FIG. 7, corresponds to the electrical chirp signal. Whether the intensity change is linear is unimportant; it is only important that the frequency of the intensity change Δi of the optical chirp signal linearly changes over the time t between an upper and a lower limit value during a period of the optical chirp signal. As noted earlier, the changing operating current intensity I also leads to a slight frequency modulation of the light emanating from the laser diode 1 which is of no consequence. It is evident that the intensity change Δi in the present case does not ensue with the optical frequency but changes with the frequency of the electrical chirp signal.

The optical chirp signal emanating from the laser diode 1 proceeds to an optical fiber coupler 29 that is arranged at the distance e from the laser diode 1 and that couples the optical chirp signal into a flexible optical fiber 23 having the length d as the measuring chirp signal or measuring light signal. The distance e of the laser diode 1 from the optical fiber coupler 29 can be adjusted as needed with an adjustment unit generally referenced 30 that is in communication with the electronic calculating unit 15 via a control line 31. The measuring light signal proceeds from the optical fiber 23 accepted in the holder 51 corresponding to the optical fiber 4, into the subject 6. A flexible optical fiber 71 having the length k that is accepted in the holder 52 corresponding to the optical fiber 7, conducts that part of the measuring light signal transmitted through the subject 6 and emerging therefrom in the region of its light entry zone to the optics 10 from which it proceeds to the photomultiplier 11. In a manner (not shown) analogous to the measuring arrangements according to FIGS. 1 and 4, moreover, the optical fibers 23 and 71 can be replaced by optical fibers having a different length and/or different materials, for the purposes recited with respect to the measuring arrangements according to FIGS. 1 and 4. There is also the possibility of varying the length of the electrical line 72 and/or of the electrical line 73, whereby the former serves the purpose of supplying the electrical chirp signal to the laser diode 1 and the latter serves the purpose of supplying that electrical output signal of the photomultiplier 11, representing the parts of the measuring light signal transmitted through the subject 6, to one input of an electrical mixer 74. In detail, the lengths of the lines 72 or 73 can be switched in three stages between the values o, o′, o″ or, respectively, p, p′, p″ with respective switches 75 or 76.

Another significant difference of the measuring arrangement of FIG. 6 compared to those set forth earlier is that the electrical chirp signal generated by the signal generator 70, rather than a light signal, that is employed as the reference chirp signal. This is supplied to the other input of the mixer 74 via a line 32. The length thereof—and thus the transit time of the reference chirp signal—can be switched between the values f, f′, f″ in three steps dependent on the switch position of a switch 33. The output signal of the mixer 74 proceeds to the filter unit 53 set forth in conjunction with the measuring arrangement according to FIG. 4 and proceeds from the filter unit 53 to the calculating unit 15 via the amplifier 13 and the analog-to-digital converter 14.

As a consequence of dispersion phenomena in the subject 6, the light received with the optical fiber 71 is a mix of optical chirp signals that are chronologically offset relative to one another. As already set forth, this signal is converted into a corresponding electrical signal with the optics 10 and of the photomultiplier 11. This electrical signal consists of electrical chirp signals that correspond to the optical chirp signals and which are chronologically offset relative to one another and is supplied to one input of the mixer 74. The mixer superimposes this electrical signal with the electrical reference chirp signal to form an electrical superposition signal which includes a mix of electrical beat signals that arise due to superimposition of the individual electrical chirp signals contained in the output signal of the photomultiplier 11 with the electrical reference chirp signal. Both the frequency of the current of the electrical reference chirp signal and the frequency of the intensity change of the measuring light signals applied to the subject 6 (and thus the frequency of the intensity of the parts of the measuring light signal transmitted through the subject 6) change linearly over time, as described above. The results in the beat frequencies of the individual electrical beat signals being directly proportional to the optical path length which that part of the measuring optical signal represented in the respective electrical beat signal, and transmitted through the subject 6, traversed in the subject 6. The degrees of modulation of the individual electrical beat signals have a direct relationship to the amplitudes or to the intensities of the parts of the measuring light signal transmitted through the subject 6 that are respectively represented in the electrical beat signals. The electrical beat signals contained in the electrical superposition signals supplied by the mixer 74 thus represent the parts of the measuring light signal introduced into the subject 6 that are transmitted through the subject 6, in terms of their optical path length traversed in the subject 6 and in terms of their intensity.

Since the amplitudes of the electrical chirp signals contained in the output signal of the photomultiplier 11 are substantially lower than those of the electrical reference chirp signal, moreover, it can be expedient for obtaining an improved signal quality to amplify the output signal of the photomultiplier 11 and/or to attenuate the electrical reference chirp signal (in any suitable manner, not shown) before the superimposition ensues in the mixer 74, since an enhanced degree of modulation of the electrical beat signals, and thus a better signal quality, can thereby be achieved.

The lower limit frequency of the filter unit 53 to which the output signal of the mixer 74 is supplied is selected (based on the transit time of the electrical reference chirp signal and the transit time of the measurement chirp signal outside the subject 6) so that electrical beat signal that represent the parts of the measuring light signal that have taken the direct path through the subject 6 (shown in broken lines in FIG. 4) have a beat frequency that is at least equal to the lower limit frequency. The transit time of the electrical reference chirp signal corresponds to the transit time of this signal from the output of the signal generator 70 to the corresponding input of the mixer 74, and is thus dependent on the length of the line 32 that is set with the switch 33. The transit time of the measurement chirp signal outside the subject 6 is the sum of the transit times of the electrical chirp signal from the output of the signal generator 70 to the laser diode 1 (which is dependent on the length of the line 72 set with the switch 75), transit time of the measuring light signal from the laser diode 1 to the optical fiber coupler 29 (which is dependent on the length of the spacing e that has been set), the transit time of the measuring light signal to the optical fiber 23, (which is dependent on the length d thereof and on the optical refractive index of its material), the transit time of those parts of the measuring light signal that have emerged from the subject 6 through the optical fiber 71 and the optics 10 to the photomultiplier 11 (which is dependent on the length k of the optical fiber 71 and the refractive index thereof as well as on the design of th optics 10 and its spacing from the photomultiplier 11), and the transit time of the output signal of the photomultiplier 11 through the line 73 to the corresponding input of the mixer 74 (which is dependent on the length of the line 73 set with the switch 76). As in the case of FIG. 4, the upper limit frequency of the filter unit 53 corresponds to the maximum optical path length (which is represented by the electrical beat signals contained in the electrical superposition signal) which parts of the measuring light signal transmitted through the subject 6 will have traversed in the subject 6, so that the electrical beat signals representing these parts of the measuring light signal can still pass the filter unit 53. Only those electrical beat signals which represent parts of the measuring light signal transmitted through the subject 6 whose running path proceeds within a cigar-shaped region 56, shown with broken lines in FIG. 6, can thus pass the filter unit 53. The length of the generated boundary line of the cigar-shaped region 56 corresponds to the maximum optical path length in the subject 6 (as does the diameter g of the cigar-shaped region), is defined by the upper limit frequency of the filter unit 53.

In the case of the measuring arrangement of FIG. 6 as well, it is evident that the transit times of the electrical reference chirp signal and of the measuring chirp signal outside the subject 6 under examination must differ by a sufficient extent in order to prevent electrical beat signals that arise due to the superimposition of the optical chirp signals contained in the output signal of the photomultiplier 11 with themselves from passing the filter unit 53.

Frequencies between 0.1 and 100 MHz are recommended for the modulation frequency of the electrical chirp signal. Frequencies between 1 MHz and 1 GHz are expedient for the center frequency of the frequency sweep of the electrical chirp signal. When the product of modulation frequency and center frequency is greater than $10^{12}$ Hz$^2$ and the frequency sweep is less than 0.5% of the center frequency, topical resolutions on the order of magnitude of 1 mm can be achieved. Consequently, the center frequency must exceed 1 MHz for a required topical resolution of 1 mm and a modulation frequency of 1 MHz. If a center frequency of 10 MHz is selected, the frequency sweep of the electrical chirp signal may amount at most to 0.05 MHz. Proceeding from 9.975 MHz, the frequency of the current of the electrical chirp signal thus changes to 10.025 MHz during a period of the electrical chirp signal; the frequency change ensues linear over the time. The analogous case applies to the intensity change $\Delta i$ of the light.

Of course, a slice of the subject 6 can also be scanned with the measuring arrangement of FIG. 6 in the way set forth in conjunction with FIG. 4 and a numerical or graphic display of a two-dimensional absorption array obtained this way in transmission mode can be made.

Analogous to the measuring arrangement of FIG. 4, the measuring arrangement of FIG. 6 can also be operated in a reflection mode when the optical fiber 71—as indicated with broken lines in FIG. 6—is introduced into a bore 77 proceeding parallel to the bore of the holder 51 that accepts the optical fiber 23.

Figure 8:
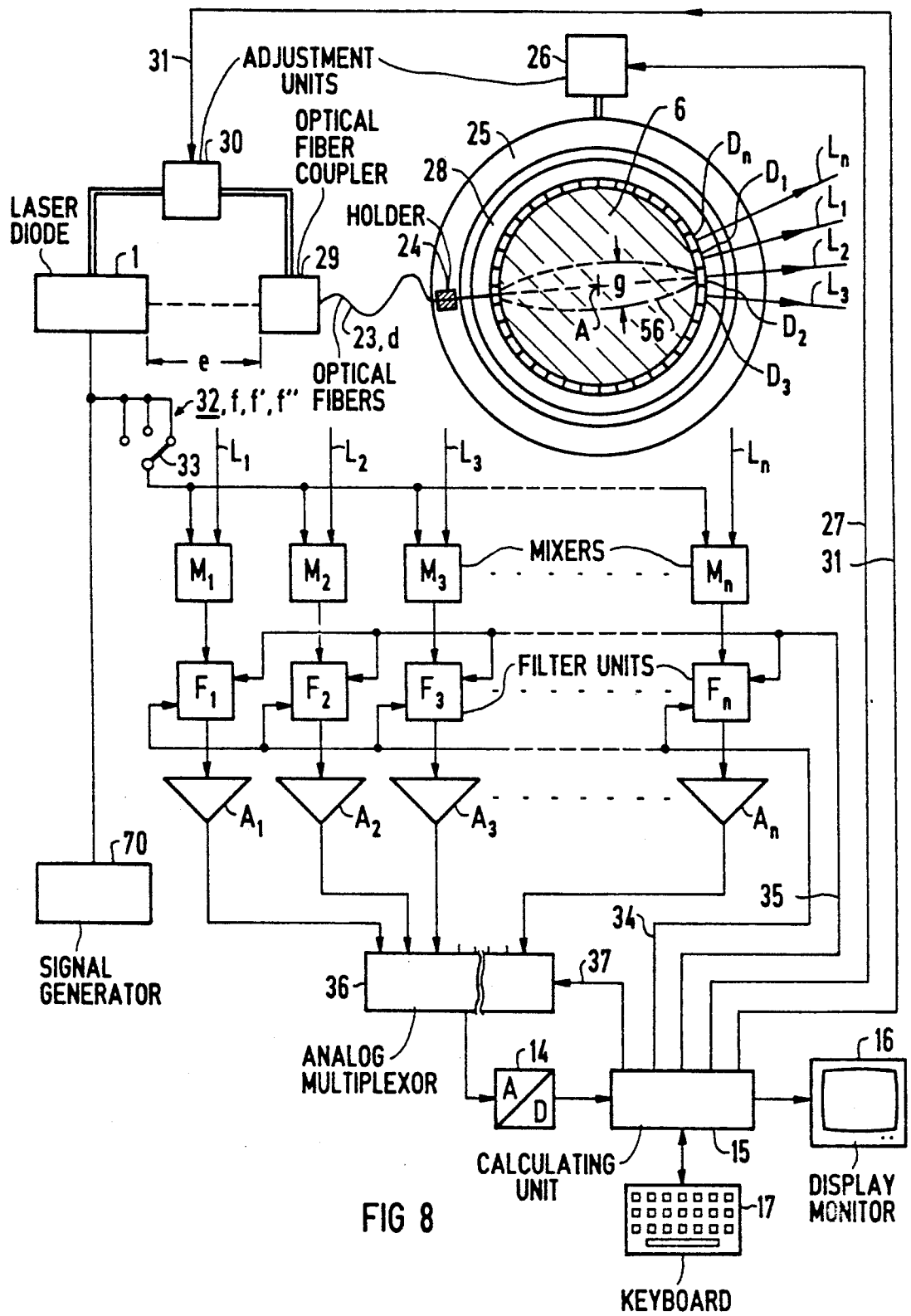
FIGS. 8 through 10 are respective block circuit diagrams of further embodiments of measuring arrangements of the invention preferably operated according to the transmission principle.

The light transmitted through the subject 6 is also detected in the measuring arrangement of FIG. 8. To that end, the optical measuring signal is again supplied to the subject 6 via a light guide, namely via the flexible optical fiber 23 having the length d. This time, however, this is attached with a holder 24 to a ring 25 that is rotatable around an axes A proceeding perpendicular to the plane of the drawing. An adjustment unit 26 is allocated thereto which is in communication with the electronic calculating unit 15 via a control line 27. As needed, the electronic calculating unit 15 actuates the adjustment unit 26 such that it turns the ring 25—and the optical fiber 23 together with it—around the axis A through a full 360°. In order to be able to detect the parts of the measuring light signal transmitted through the subject 6, a detector is provided that is formed by an annular array of n detector units, in the form of identical photodiodes $D_1$, $D_2$, $D_3$, ... $D_n$ that are attached to a stationary ring 28. In the case of the measuring arrangement shown in FIG. 8, n=36.

The ring 28, which is coaxial with the ring 25, surrounds the subject 6, for example a female breast, preferably such that the photodiodes $D_1$ through $D_n$ are located in close proximity to the surface of the subject 6 and, as shown, preferably press thereagainst. The light-sensitive sensor surfaces of the photodiodes $D_1$ through $D_n$, that form the light entry zones of the measuring arrangement, face toward the surface of the subject 6. The optical fiber 23 is attached to the ring 25 with the holder 24 so that its end, forming the light exit zone and which extends up to the immediate proximity of the surface of the subject 6, is located next to the annular array of photodiodes $D_1$ through $D_n$, offset in the direction of the axis A. The end of the optical fiber 23 accepted in the holder 24 is aligned such that its center axis intersects the axis A at an angle that is dimensioned such that the center axis—after completion of one adjustment step of the ring 25—proceeds centrally through the sensor surface of that photodiode lying diametrically opposite the end of the optical fiber 23, which is the photodiode $D_2$ in the case of FIG. 4. The step-by-step rotation of the ring 25 ensues in angular steps of 360°/n. The measuring chirp signal supplied to the subject 6 as the measuring light signal is generated as set forth in conjunction with the measuring arrangement of FIG. 6. The laser diode 1 is thus again driven with an electrical chirp signal from the signal generator 70.

The optical chirp signal proceeding from the laser diode 1 proceeds to the subject 6 via an optical fiber coupler 29 that is arranged at the variable spacing e from the laser diode 1 and via the optical fiber 23, as set forth in conjunction with FIG. 6.

The parts of the measuring chirp signal supplied to the subject 6 with the optical fiber 23 as the measuring light signal, which are transmitted through the subject 6 are incident on the light-sensitive surfaces of the photodiodes $D_1$ through $D_n$ and are converted by these photodiodes into corresponding electrical signals. These electrical signals proceed via lines $L_1$ through $L_n$, all of which have the same length, to respective first inputs of a plurality of identical electrical mixers $M_1$ through $M_n$, whereby the plurality of mixers corresponds to the plurality of photodiodes and one mixer is allocated to each photodiode.

The electrical chirp signal respectively generated with the signal generator 70 is supplied to the respective second inputs of the mixers $M_1$ through $M_n$ as the electrical reference chirp signal via the line 32. The length thereof, and thus the transit time of the electrical reference chirp signal, can be adjusted in three steps f, f1, f'' dependent on the switch position of a switch 33. The electrical output signals of the mixers $M_1$ through $M_n$ respectively proceed to identical filter units $F_1$ through $F_n$. The filter units $F_1$ through $F_n$ each have an amplitude frequency response corresponding to that of the filter unit 53 previously described which has a trailing edge below as well as above an upper limit frequency. The filter units $F_1$ through $F_n$ thus each contain a low-pass filter and a high-pass filter that are connected in succession. The limit frequencies of the filter units $F_1$ through $F_n$ can be adjusted with the electronic calculating unit 15 via control lines 34 and 35, so that all filter units $F_1$ through $F_n$ have the same upper limit frequency and the same lower limit frequency. The upper and the lower limit frequencies can coincide, resulting in the filter units $F_1$ through $F_n$ then having a band-pass characteristic.

Each filter unit $F_1$ through $F_n$ is followed by an identical amplifier $A_1$ through $A_n$. The respective output signals of the amplifiers $A_1$ through $A_n$ proceed to the inputs of an n-to-one analog multiplexer 36 whose output is connected to the electronic calculating unit 15 via the analog-to-digital converter 14. The calculating unit 15 controls the multiplexer 36 via a control line 37, based on the angular position of the ring 25. This control results in a series of electrical superposition signals, each arising by mixing the output signal of the photodiode currently lying diametrically opposite the light exit zone of the optical fiber 23 with the reference chirp signal proceeding to the analog-to-digital converter 14 via the corresponding filter unit, the corresponding amplifier and the corresponding channel of the multiplexer 36. In the case of FIG. 8, the ring 25 assumes such a position that the photodiode D lies diametrically opposite the light exit zone of the optical fiber 23. For the illustrated position of the ring 25, consequently, the electronic calculating unit 15 controls the multiplexer 36 such that the output signal of the amplifier $A_2$, to which the electrical superposition signal obtained by mixing the electrical output signal of the photodiode $D_2$ with the electrical reference chirp signal in the mixer $M_2$ and filtered with the filter unit $F_2$, proceeds to the input of the analog-to-digital converter 14. For clarity, only the lines $L_1$, $L_2$, $L_3$, $L_n$, the mixers $M_1$, $M_2$, $M_3$, $M_n$, the filter units $F_1$, $F_2$, $F_3$, $F_n$ and the amplifiers $A_1$, $A_2$, $A_3$, $A_n$ are shown in FIG. 8.

The measuring light signal introduced into the subject with the optical fiber 23 is dispersed, resulting in the light being partially transmitted through the subject 6, whereby one part of the transmitted light emerges from the subject 6 in the region of the light-sensitive surface of the photodiode—the photodiode $D_2$ in the case of FIG. 8—lying diametrically opposite the light exit zone of the optical fiber 23, dependent on the current position of the ring 25. In the same way as set forth in greater detail in conjunction with FIG. 6, the electrical signal acquired from the electrical output signal of the respective photodiode, following superimposition with the electrical reference chirp signal in the respective mixer to form the corresponding electrical superposition signal and filtering in the corresponding filter unit, represents those parts of the measuring light signal that have taken a path through the subject 6 proceeding within a cigar-shaped region 56 having the diameter g which is shown in FIG. 8. Based on the transit time of the electrical reference chirp signal (which is dependent on the position of the switch 33) and the transit time of the measuring chirp signal outside the subject 6 (which is dependent on the spacing e which has been set) the lower limit frequency of the filter units $F_1$ through $F_n$ is selected such that electrical beat signals, which represent parts of the measuring light signal that have taken the direct path through the subject 6 (shown with broken lines in FIG. 8) have a beat frequency that is at least equal to the lower limit frequency. The upper limit frequency of the filter units $F_1$ through $F_n$ is selected such that the desired diameter g of the cigar-shaped region 56 results. The transit time of the electrical reference chirp signal corresponds to the transit time of the signal from the output of the signal generator 70 to the input of the respective mixer. Differing from what is shown in FIG. 8 for simplicity, it must be assured that the lines to the mixers $M_1$ through $M_n$ are equal in length in order to achieve respectively identical transit times of the electrical reference chirp signal. The transit time of the measuring chirp signal outside the subject 6 arises from the sum of the transit time of the electrical chirp signal from the output of the signal generator 70 to the laser diode 1 (which is dependent on the corresponding line length), the transit time of the optical chirp signal from the laser diode 1 to the optical fiber coupler 29 (which is dependent on the length of the spacing e which has been set), the transit time of the measuring light signal through the optical fiber 23 (which is dependent on the length d thereof and on the optical refractive index of its material), and the transit time of the output signal of the respective photodiode through the corresponding line to the respective mixer.

A slice of the subject 6 can also be scanned and a numerical or graphic display of a two-dimensional absorption array calculated in this way in the transmission mode can also be undertaken with the measuring arrangement of FIG. 8. Based on the length of the line 32 that has been set with the switch 33 and the spacing e which has been set, the electronic calculating unit 15 sets the upper limit frequency of the filter units $F_1$ through $F_n$ such that the desired diameter g of the cigar-shaped region 56 arises. The lower limit frequency (which the filter units $F_1$ through $F_n$ need not absolutely have for the transmission mode but which is advantageous for the suppression of noise signals that, for example, can be caused by stray light) is set by the electronic calculating unit 15 such that beat signals that represent parts of the measuring light signal that have taken the direct path through the subject can just still pass. For the purpose of a scan motion, the electronic calculating unit 15 then adjusts the ring 25, relative to the ring 28 having the photodiodes $D_1$ through $D_n$ and relative to the subject 6, in steps such that the light exit zone of the optical fiber 23 is first aligned to the photodiode $D_1$, then to the photodiode $D_2$, etc., until it is aligned to the photodiode $D_n$. Simultaneously, the electronic calculating unit 15 controls the multiplexer 36 such that the output of that filter unit among the filter units $F_1$ through $F_n$ corresponding to the photodiode among photodiodes $D_1$ through $D_n$ to which the light exit zone of the optical fiber 23 is currently aligned, is connected to the analog-to-digital converter 14. The electronic calculating unit 15 stores the output data of the analog-to-digital converter 14 arising during this scan event and calculates the absorption array to be displayed on the monitor 16 therefrom.

Figure 9:
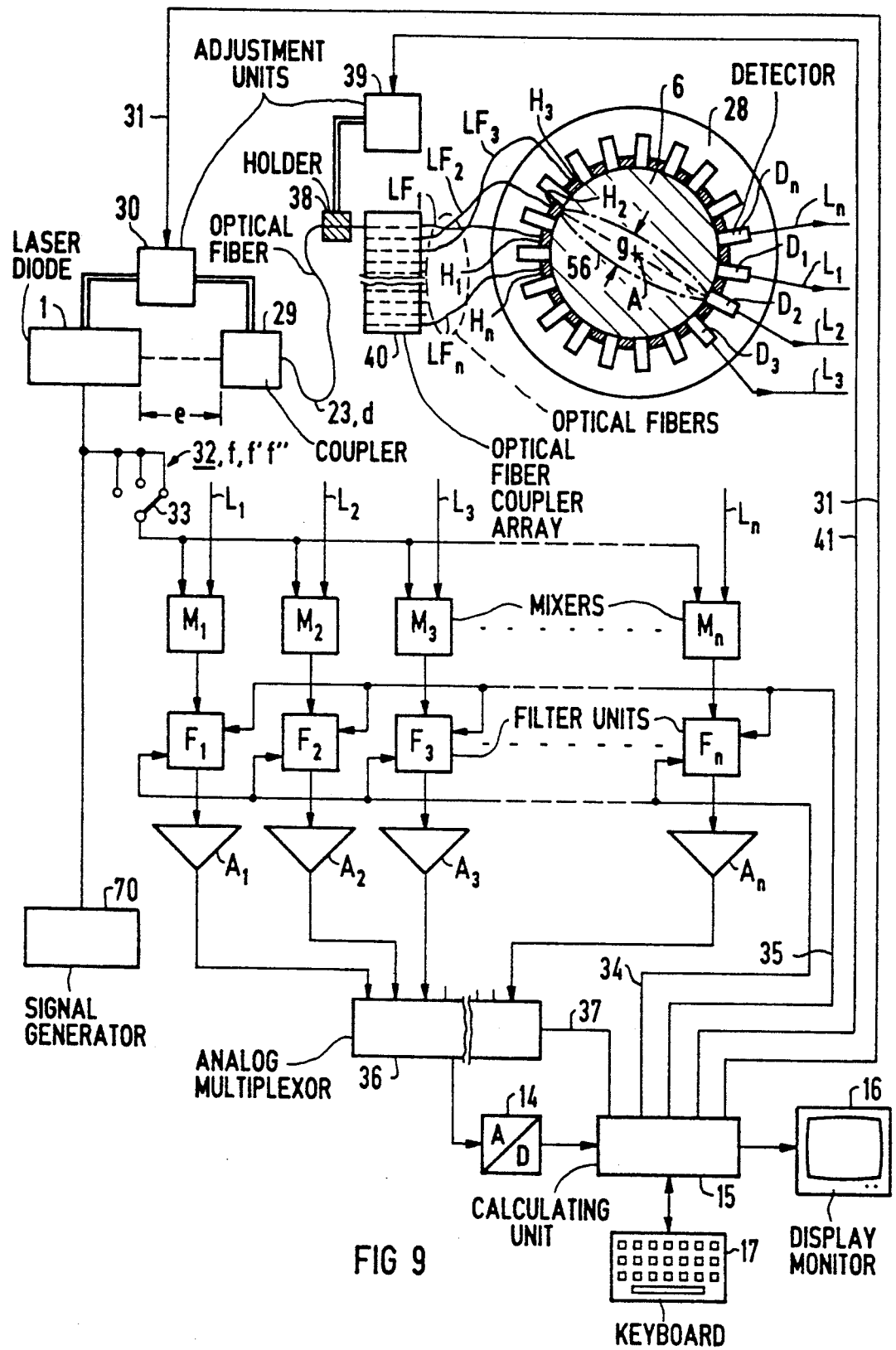

The measuring arrangement according to FIG. 9 essentially differs from that of FIG. 8 in that the ring 25 and the adjustment unit 26 allocated thereto are omitted. Instead, the optical fiber 23 is accepted in a holder 38 which can be linearly adjusted step-by-step with an adjustment unit 39 such that the light exit zone of the optical fiber 23 can be moved past, for example, a linear optical fiber coupler array 40 step-by-step. The measuring light signal from the laser diode 1 is successively coupled as a measuring chirp signal into one of n optical fibers $LF_1$ through $LF_n$, having the same length, each having one end connected to the optical fiber coupler array 40. The other ends of the optical fibers $LF_1$ through $LF_n$, which form the light exit zones of the measuring arrangement, are accepted in holders $H_1$ through $H_n$ and are secured to the stationary ring 78 surrounding the subject 6, for example a female breast. The optical fibers $LF_1$ through $LF_n$ are preferably secured thereto such that their light exit zones are situated close to the surface of the subject 6, as shown. The holders $H_1$ through $H_n$ and the photodiodes $D_1$ through $D_n$ are attached to the ring 78 in alternation. The coinciding number of optical fibers $LF_1$ and $LF_n$ and photodiodes $D_1$ through $D_n$ is selected such that the light exit zone of an optical fiber $LF_1$ through $LF_n$ lies diametrically opposite the light-sensitive sensor surface of a photodiode $D_1$ through $D_n$. The ends of the optical fibers $LF_1$ through $LF_n$ are accepted such in the holders $H_1$ through $H_n$ so that the center axis of each optical fiber proceeds through the middle of the photodiode $D_1$ through $D_n$ respectively lying diametrically opposite. In the case of FIG. 9, n=19.

The electronic calculating unit 15 controls the adjustment unit 39 and the multiplexer 36 via the respective control lines 41 and 37 such that the output of that filter unit among filter units $F_1$ through $F_n$ which corresponds to the photodiode among photodiodes $D_1$ through $D_n$ which lies diametrically opposite the light exit zone of that optical fiber $LF_1$ through $LF_n$ into which the measuring light signal is currently coupled with the optical fiber 23 and the optical fiber coupler array 40 is connected to the analog-to-digital converter 14. When, as shown in FIG. 9, for example, the measuring light signal is coupled into the optical fiber $LF_2$, the output signal of the amplifier $A_2$ belonging to the photodiode $D_2$ lying diametrically opposite the optical fiber $LF_2$ proceeds via the multiplexer 36 to the analog-to-digital converter 14.

When a two-dimensional absorption array of the subject 6 is to be identified with the measuring arrangement of FIG. 9, the electronic calculating unit 15 adjusts the holder 38 such that the measuring light signal is successively coupled into the optical fibers $LF_1$ through $LF_n$. Synchronized therewith, the electronic calculating unit 15 controls the multiplexer 36 such that the output signal of the corresponding amplifier $A_1$ through $A_n$ respectively proceeds to the analog-to-digital converter 14. The digital output data thereof arising during this scan event are stored by the electronic calculating unit 15 and the electronic calculating unit 15 calculates the absorption array therefrom, which is then displayed in a suitable form on the monitor 16.

The transit time of the measuring chirp signal, corresponds to the sum of the transit times of the electrical chirp signal from the signal generator 70 to the light source 1, the transit time of the measuring light signal over the distance e to the optical fiber coupler, through the optical fiber 23 and the respective optical fiber $LF_1$ through $LF_n$, and the transit time as well as of the output signal of the respective photodiode $D_1$ through $D_n$ through the corresponding line $L_1$ through $L_n$ to the associated mixer $M_1$ through $M_n$. The transit time of the measuring light signal in the respective optical fiber $LF_1$ through $LF_n$ is dependent on the length thereof and on the refractive index of its material, which are the same for all optical fibers $LF_1$ through $LF_n$. The transit time of the output signal of the respective photodiode is dependent on the length of the lines $L_1$ through $L_n$.

Figure 10:
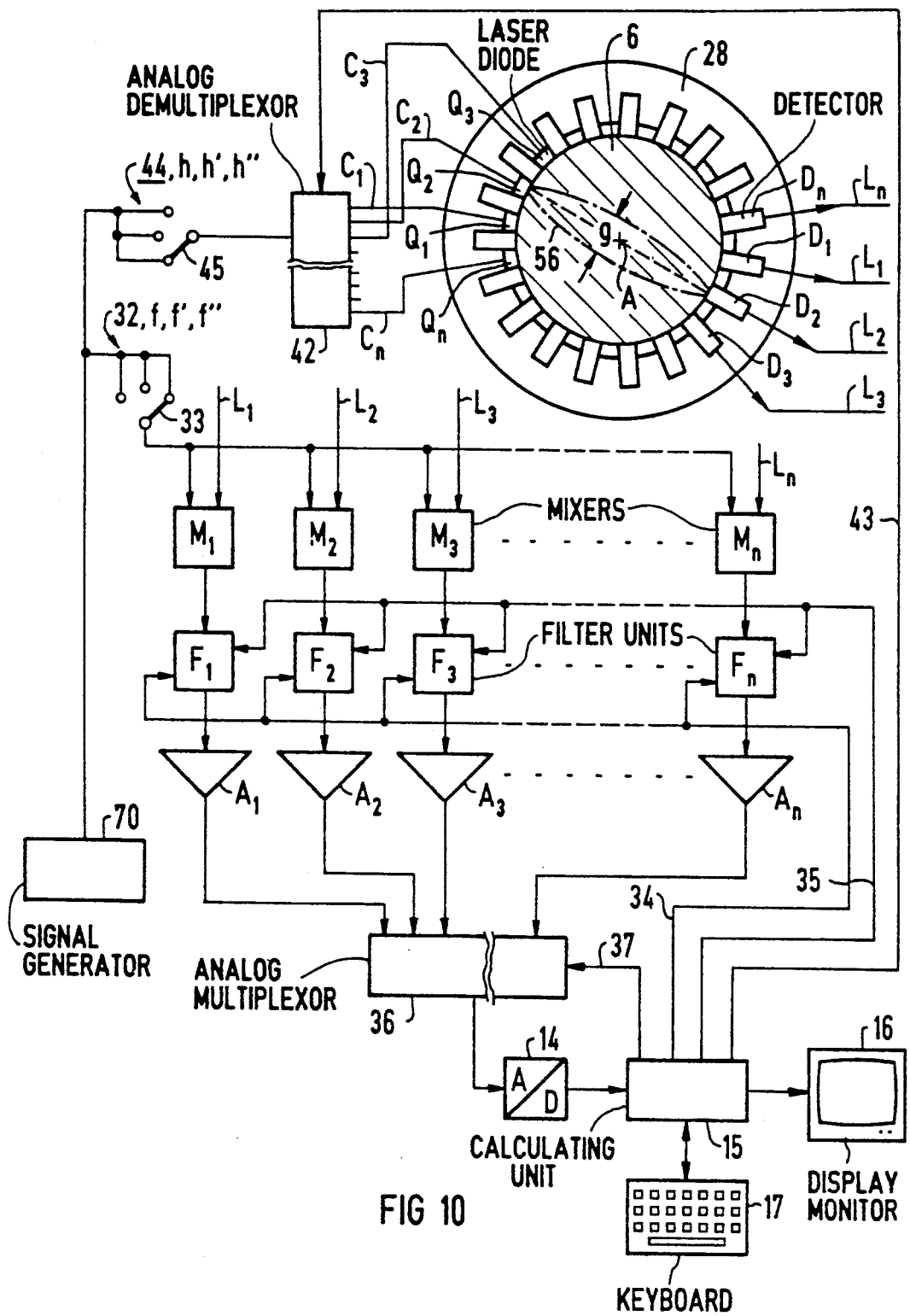

The measuring arrangement according to FIG. 10 differs from that according to FIG. 9 again in that laser diodes $Q_1$ through $Q_n$ are attached to the ring 78 instead of the light exit zones of the optical fibers $LF_1$ through $LF_n$ between the photodiodes $D_1$ through $D_n$. As shown, the laser diodes $Q_1$ through $Q_n$, have light exit zones which form those of the measuring arrangement, preferably situated close to the surface of the subject 6, for example a female breast. These light exit zones are connected via lines $C_1$ through $C_n$ of identical length to the outputs of a one-to-n analog demultiplexer 42 that is controlled via a line 43 by the electronic calculating unit 15. The electrical chirp signal generated with the signal generator 70 is supplied to the input of the multiplexer 42 via the line 44 as the measuring chirp signal that is supplied to one of the laser diodes $Q_1$ through $Q_n$ dependent on the control information proceeding to the demultiplexer 42 from the electronic calculating unit 15 via the control line 43. In a manner analogous to FIGS. 8 and 9, the electronic calculating unit 15 controls the multiplexer 36 such that the output of that amplifier $A_1$ through $A_n$ to which the photodiode $D_1$ through $D_n$ which is respectively driven with the electrical chirp signal (and which thus lies opposite the laser diode $Q_1$ through $Q_n$ outputting the measuring light signal) is allocated is respectively connected to the analog-to-digital converter 14. When the control of the multiplexer 36 and of the demultiplexer 42 ensues such that the laser diodes $Q_1$ through $Q_n$ transmit the optical measuring signal into the subject 6 in succession and the output signals of the respectively corresponding amplifier among amplifiers $A_1$ through $A_n$ proceed to the analog-to-digital converter 14, the electronic calculating unit 15 can calculate an absorption array from the data collected during this scan event. In the case of FIG. 10, as well, n=19.

In order to enable a matching of the transit time of the measuring chirp signal outside the subject under examination to the current conditions, moreover, there is the possibility of adjusting the length of the line 44 in three steps h, h', h" by actuating the switch 45. The transit time of the measuring chirp signal, moreover, is also dependent on the length of the lines $C_1$ through $C_n$ and on the length of the lines $L_1$ through $L_n$ in addition to being dependent on the length of the line 44 that has been set.

The measuring arrangements of FIGS. 8, 9 and 10 can also be operated in a reflection mode when the electronic calculating unit 15 controls the multiplexer 36 such that the output signal of one of the photodiodes that are situated immediately next to the optical fiber 23 or the optical fiber $LF_1$ through $LF_n$ respectively emitting the measuring light signal, or laser diode $Q_1$ through $Q_n$, is utilized for forming the superposition signal and the superposition signal formed in this way is supplied to the analog-to-digital converter 14 via the corresponding filter unit and via the corresponding amplifier. It is thereby recommendable to set the limit frequencies of the filter units $F_1$ through $F_n$ such that they coincide, i.e. such that a band-pass characteristic derives. By gradually varying the center frequency of the band-pass characteristic that has been set for the purpose of raising the center frequency, annular section planes of the subject 6 can be scanned, their respective diameters decreasing with increasing center frequency.

A three-dimensional scanning of the subject 6 can also be achieved with the described measuring arrangements. In the case of the measuring arrangement of FIGS. 1 and 5, a scan motion in the direction of an axis preferably intersecting the longitudinal axis of the slot 22 at a right angle must additionally ensue for this purpose. In the case of the measuring arrangements of FIGS. 4, 6 and 8-10, a scan motion in the direction of the axis A must additionally ensue.

In the comments directed to the measuring arrangements according to FIGS. 6 and 8-10, the signal transit times in the laser diode 1 in the laser diodes $Q_1$ through $Q_n$, in the optical fiber coupler 29, in the optical fiber coupler array 40, in the analog demultiplexer 42 and in the optics 10, in the photomultiplier 11 and in the photodiodes $D_1$ through $D_n$ were not discussed. If significant transit times arise in those components, these, of course, must be taken into consideration when setting the spacing e and/or when setting the center frequency of the band-pass filter 12 or the limit frequencies of the filter units 53 or $F_1$ through $F_n$.

In order to be able to implement spectroscopic measurements, i.e. in order to be able to identify absorption coefficients for different wavelengths of the light introduced into the subject 6, a plurality of monochromatic light sources having different wavelengths can be provided in the measuring arrangements according to FIGS. 1 and 4-6. The monochromatic light sources are connectable to the signal generator 2 (or 70) and can be aligned one at a time vis-a-vis the optical fiber fan-out coupler 3 (or the optical fiber coupler 29 or the semireflective mirror 60) such that the light from the coupled monochromatic source is supplied to the subject 6 via the optical fiber 4 (or 23), through the semi-reflective mirror 60 or via the optical fibers $LF_1$ through $LF_n$. There is also the further possibility in the case of FIGS. 1 and 4-6 of employing one light source that can be operated for outputting monochromatic light having different wavelengths. Finally, there is also the possibility in all measuring arrangements which have been set forth of providing a light source or light sources that output polychromatic light and to provide interchangeable optical filters between light source or sources and the subject and/or between the subject and the detector. These optical filter means permit only monochromatic light of a wavelength passed by the selected filter to proceed to the subject, or to proceed from the subject to the detector means.

Although modifications and changes may be suggested by those skilled in the art, it is the intention of the inventors to embody within the patent warranted hereon all changes and modifications as reasonably and properly come within the scope of their contribution to the art.

We claim as our invention:
1. An apparatus for optically analyzing tissue in vivo comprising:
   means for directing a measuring chirp signal at a tissue-containing subject, said measuring chirp signal being a coherent optical signal of light selected from the group consisting of visible, NIR and IR light, a part of said measuring chirp signal emerging from said subject after interacting therein with tissue to be analyzed and forming an emerging signal;
   means for generating a reference chirp signal having a defined phase relationship to said measuring chirp signal;
   means for superimposing said emerging signal with said reference chirp signal to form a superposition signal having sets of beats, each set of beats having a respective beat frequency;
   filter means, for receiving said superposition signal and having a transmission range with an upper limit frequency, for generating from said superposition signal a filtered signal having at least one beat frequency within said transmission range; and
   means for dimensioning parameters including the transit time of said measuring chirp signal outside said subject, the transit time of said reference chirp signal, and said upper limit frequency of said filter means for causing said filtered signal to represent substantially only parts of said emerging signal which have traversed an optical path length in said subject which does not exceed a defined maximum optical path length.

2. An apparatus as claimed in claim 1 wherein said filter means is a filter means having a transmission range which also has a lower limit frequency, and wherein said lower limit frequency is among said parameters dimensioned by said means for dimensioning.

3. An apparatus as claimed in claim 2 further comprising: means for varying at least one of said parameters.

4. An apparatus as claimed in claim 2 further comprising:
   evaluation means, for receiving said filtered signal, for calculating said optical path length traversed in said subject by said parts of said emerging signal represented in said filtered signal, based on said upper and lower limit frequencies of said filter means, said transit time of said measuring chirp signal outside said subject, and said transit time of said reference chirp signal.

5. An apparatus as claimed in claim 1 wherein said means for generating said measuring chirp signal and said means for generating said reference chirp signal comprise, in combination, at least one coherent light source, and wherein said apparatus further comprises:
   signal generator means for generating a signal for frequency-modulating light from said coherent light source for causing said coherent light source to emit an optical chirp signal having an optical frequency varying in a defined manner over time;
   beam splitter means for splitting said optical chirp signal into a first optical signal forming said measuring chirp signal and a second optical signal forming said reference chirp signal;
wherein said means for superimposing is a means for optically superimposing said measuring chirp signal and said reference chirp signal to form an optical superposition signal, and wherein said apparatus further comprises:

opto-electronic detector means for detecting said optical superposition signal and converting it into an electrical signal which is supplied to said filter means as said superposition signal.

6. An apparatus as claimed in claim 1 wherein said means for generating said measuring chirp signal and said means for generating said reference chirp signal comprise, in combination, at least one coherent light source, and wherein said apparatus further comprises:

signal generator means for generating a signal for amplitude-modulating light from said coherent light source for causing said coherent light source to emit an optical chirp signal having an optical intensity changing over time at a frequency varying in a defined manner over time;

beam splitter means for splitting said optical chirp signal into a first optical signal forming said measuring chirp signal and a second optical signal forming said reference chirp signal;

wherein said means for superimposing is a means for optically superimposing said measuring chirp signal and said reference chirp signal to form an optical superposition signal, and wherein said apparatus further comprises:

opto-electronic detector means for detecting said optical superposition signal and converting it into an electrical signal which is supplied to said filter means as said superposition signal.

7. An apparatus as claimed in claim 5 or 6 wherein said beam splitter means and said means for superimposing, in combination, consist of a semi-reflective mirror onto which said optical chirp signal from said coherent light source is incident at an angle deviating from 90° thereby splitting said optical chirp signal into said measuring chirp signal and said reference chirp signal, propagating along different respective propagation paths, and reflector means, disposed in the propagation path of said reference chirp signal, for directly reflecting said reference chirp signal back along said propagation path.

8. An apparatus as claimed in claim 5 or 6 wherein said beam splitter means is an optical fiber fan-out coupler and wherein said means for superimposing is an optical fiber fan-in coupler, and said apparatus further comprising:

a first optical fiber conducting said reference chirp signal from said optical fiber fan-out coupler to said optical fiber fan-in coupler;

a second optical fiber conducting said measuring chirp signal from said optical fiber fan-out coupler to said subject; and a third optical fiber conducting said emerging signal to said optical fiber fan-in coupler.

9. An apparatus as claimed in claim 1 wherein said means for generating said measuring chirp signal is a coherent light source, wherein said means for generating said reference chirp signal is an electrical generator means for generating a first electrical signal forming said reference chirp signal and being connected to said coherent light source for causing said coherent light source to emit an amplitude-modulated signal, forming said measuring chirp signal, having an optical intensity changing over time at a frequency varying in a defined manner over time, and wherein said apparatus further comprises:

opto-electronic detector means for converting said emerging signal into a second electrical signal, forming an electrical emerging signal, and wherein said means for superimposing is a mixer means, supplied with said reference chirp signal and said electrical emerging signal, for generating a third electrical signal, forming said superposition signal, which is supplied to said filter means.

10. An apparatus as claimed in claim 9 wherein said means for directing said measuring chirp signal at said subject has a light exit zone from which said optical chirp signal exits toward said subject, and wherein said detector means has a light entry zone into which said emerging signal enters said detector means, said light exit zone and said light entry zone being disposed on opposite sides of said subject, and said apparatus further comprising means for generating relative movement between said light exit and light entry zones, in combination, and said subject for scanning said subject.

11. An apparatus as claimed in claim 10 wherein said detector means is formed by at least one photodiode.

12. An apparatus as claimed in claim 10 wherein said detector means is formed by at least one photomultiplier.

13. An apparatus as claimed in claim 9 wherein said means for directing said measuring chirp signal at said subject has a light exit zone from which said optical chirp signal exits toward said subject, and wherein said detector means has a light entry zone into which said emerging signal enters said detector means, said light exit zone and said light entry zone being disposed in close proximity on the same side of said subject, and said apparatus further comprising means for generating relative movement between said light exit and light entry zones, in combination, and said subject for scanning said subject.

14. An apparatus as claimed in claim 9 wherein said means for directing said measuring chirp signal at said subject has a light exit zone from which said optical chirp signal exits toward said subject, wherein said detector means consists of a plurality of separate detector elements, each detector element having a light entry zone into which a part of said emerging signal enters that detector element, and said apparatus further comprising means for generating a relative movement between said light exit zone and said subject for scanning said subject, and multiplexer means for successively connecting said individual detector elements to said means for superimposing during said scanning.

15. An apparatus as claimed in claim 14 wherein said detector elements are annularly disposed around said subject.

16. An apparatus as claimed in claim 15 wherein said light exit zones are annularly arranged around said subject in alternation with said detector elements.

17. An apparatus as claimed in claim 10, 13 or 14 further comprising evaluation means for calculating an at least two-dimensional absorption array of absorption coefficients of a region of said subject from said filtered signal.

18. An apparatus as claimed in claim 17 further comprising graphic display means for displaying the calculated absorption arrays with different chromatic values respectively allocated to different absorption coefficients.

19. An apparatus as claimed in claim 17 further comprising graphic display means for displaying the calculated absorption arrays with different grayscale values respectively allocated to different absorption coefficients.

20. An apparatus as claimed in claim 9 wherein said means for directing said measuring chirp signal at said subject has a plurality of light exit zones from which said optical chirp signal exits, one at a time, toward said examination subject, wherein said detector means consists of a plurality of separate detector elements corresponding in number to said plurality of light exit zones, each detector element having a light entry zone into which a part of said emerging signal enters that detector element, each light exit zone having one detector element, and thus one light entry zone, uniquely allocated thereto, and wherein said means for directing includes means for successively directing said optical chirp signal out of each of said light exit zones for scanning said subject.

21. An apparatus as claimed in claim 20 wherein said means for directing said measuring chirp signal at said subject includes a plurality of separate optical fibers, each optical fiber having a first end and having a second end forming one of said light exit zones, an optical fiber array in which said first ends of said optical fibers are mounted, and means for moving a source of said coherent optical chirp signal through successive positions relative to said array for successively coupling said optical chirp signal into each of said first ends of said optical fibers.

22. An apparatus as claimed in claim 9 wherein said means for superimposing includes a plurality of mixers, corresponding in number to said plurality of detector elements, and said mixers being respectively connected to said detector elements for mixing the signal from the detector element connected thereto with said reference chirp signal, wherein said filter means comprises a plurality of filter elements corresponding in number to said plurality of mixers, said filter elements being respectively connected to said mixers, and said apparatus further comprising evaluation means, connected to the outputs of all of said filter elements, for calculating said optical path length traversed by said part of said emerging signal in said subject.

23. An apparatus as claimed in claim 9 wherein said means for directing said measuring chirp signal at said subject has a light exit zone from which said optical chirp signal exits toward said subject, and wherein said means for superimposing has a light entry zone into which said emerging signal enters said means for superimposing, said light exit zone and said light entry zone being disposed on opposite sides of said subject, and said apparatus further comprising means for generating relative movement between said light exit and light entry zones, in combination, and said subject for scanning said subject.

24. An apparatus as claimed in claim 1 wherein said means for directing said measuring chirp signal at said subject includes at least one laser diode as a source for said coherent optical chirp signal.

25. An apparatus as claimed in claim 1 further comprising light guide means for conducting said optical chirp signal from said means for directing to said subject.

26. An apparatus as claimed in claim 1 further comprising light guide means for conducting said emerging signal from said subject to said means for superimposing.

27. An apparatus as claimed in claim 1 further comprising detector means for detecting said emerging signal and transmitting said emerging signal to said means for superimposing, wherein said means for directing said measuring chirp signal at said subject has a light exit zone from which said optical chirp signal exits toward said subject, and wherein said detector means has a light entry zone into which said emerging signal enters said detector means, said light exit zone and said light entry zone being disposed on opposite sides of said subject, and said apparatus further comprising means for generating relative movement between said light exit and light entry zones, in combination, and said subject for scanning said subject.

28. An apparatus as claimed in claim 27 wherein said detector means is formed by at least one photodiode.

29. An apparatus as claimed in claim 27 wherein said detector means is formed by at least one photomultiplier.

30. An apparatus as claimed in claim 1 further comprising detector means for detecting said emerging signal and transmitting said emerging signal to said means for superimposing, wherein said means for directing said measuring chirp signal at said subject has a light exit zone from which said optical chirp signal exits toward said subject, and wherein said detector means has a light entry zone into which said emerging signal enters said detector means, said light exit zone and said light entry zone being disposed in close proximity on the same side of said subject, and said apparatus further comprising means for generating relative movement between said light exit and light entry zones, in combination, and said subject for scanning said subject.

31. An apparatus as claimed in claim 1 wherein said means for directing said measuring chirp signal at said subject has a light exit zone from which said optical chirp signal exits toward said subject, and wherein said means for superimposing has a light entry zone into which said emerging signal enters said means for superimposing, said light exit zone and said light entry zone being disposed on opposite sides of said subject, and said apparatus further comprising means for generating relative movement between said light exit and light entry zones, in combination, and said subject for scanning said subject.

32. An apparatus as claimed in claims 27, 30 or 31 further comprising evaluation means for calculating an at least two-dimensional absorption array of absorption coefficients of a region of said subject from said filtered signal.

33. An apparatus as claimed in claim 32 further comprising graphic display means for displaying the calculated absorption arrays with different chromatic values respectively allocated to different absorption coefficients.

34. An apparatus as claimed in claim 32 further comprising graphic display means for displaying the calculated absorption arrays with different grayscale values respectively allocated to different absorption coefficients.

35. An apparatus for optically analyzing tissue comprising:
  a coherent light source for generating a coherent optical chirp signal of light selected from the group consisting of visible, NIR and IR light;
  beam splitter means for splitting said optical chirp signal into a measuring chirp signal and a reference chirp signal having a defined phase relationship to said measuring chirp signal;

a first group of optical fibers, having respectively different combinations of refractive index and length, said optical fibers in said first group being used one at a time to conduct said measuring chirp signal from said beam splitter means to a tissue-containing subject, a part of said measuring chirp signal emerging from said subject after interacting with tissue therein to be analyzed and forming an emerging signal;

means for superimposing said emerging signal with said reference chirp signal to form an optical superposition signal having sets of beats, each set of beats having a respective beat frequency;

a second group of separate optical fibers, having respectively different combinations of refractive index and length, said optical fibers in said second group being selected for use one at time to conduct said reference chirp signal from said beam splitter means to said means for superimposing;

a third group of separate optical fibers, having respectively different combinations of refractive index and length, said optical fibers in said second group being selected for use one at a time to conduct said emerging signal from said subject to said means for superimposing;

detector means for converting said optical superposition signal into an electrical superposition signal;

filter means, for receiving said electrical superposition signal and having a transmission range with an upper limit frequency, for generating from said superposition signal a filtered signal having at least one beat frequency within said transmission range; and means for selecting said upper limit frequency, in combination with the transit time of said measuring chirp signal outside said subject defined by the selected one of said optical fibers in said first and third groups and the transit time of said reference chirp signal defined by the selected one of said optical fibers in said second group, for causing said filtered signal to represent substantially only parts of said emerging signal which have traversed an optical path length in said subject which does not exceed a defined maximum optical path length.

36. An apparatus as claimed in claim 35 wherein the selected one of said optical fibers in said first group has an end facing said subject forming a light exit zone from which said measuring chirp signal exits toward said subject and wherein the selected one of said optical fibers in said third group has an end facing said subject forming a light entry zone into which said emerging signal enters, said light entry zone and said light exit zone being disposed in close proximity on a same side of said subject.

37. An apparatus as claimed in claim 35 wherein the selected one of said optical fibers in said first group has an end facing said subject forming a light exit zone from which said measuring chirp signal exits toward said subject and wherein the selected one of said optical fibers in said third group has an end facing said subject forming a light entry zone into which said emerging signal enters, said light entry zone and said light exit zone being disposed on opposite sides of said subject.

38. An apparatus as claimed in claim 35 wherein the selected one of said optical fibers in said first group has an end facing said subject forming a light exit zone from which said measuring chirp signal exits toward said subject and wherein the selected one of said optical fibers in said third group has an end facing said subject forming a light entry zone into which said emerging signal enters, said light entry zone and said light exit zone being disposed in close proximity on a same side of said subject and said apparatus further comprising means for generating relative motion between said light entry and exit zones, in combination, and said subject for scanning said subject.

39. An apparatus as claimed in claim 35 wherein the selected one of said optical fibers in said first group has an end facing said subject forming a light exit zone from which said measuring chirp signal exits toward said subject and wherein the selected one of said optical fibers in said third group has an end facing said subject forming a light entry zone into which said emerging signal enters, said light entry zone and said light exit zone being disposed on opposite sides of said subject and said apparatus further comprising means for generating relative motion between said light entry and exit zones, in combination, and said subject for scanning said subject.

40. An apparatus for optically analyzing tissue in vivo comprising:

a coherent light source generating a coherent optical chirp signal of light selected from the group consisting of visible, NIR and IR light, said optical chirp signal propagating along a first propagation path;

a semi-reflective mirror disposed in said first propagation path at an angle deviating from 90° which splits said optical chirp signal into a measuring chirp signal which continues to propagate along said first propagation path toward a tissue-containing subject, and a reference chirp signal propagating along a second propagation path, different from said first propagation path, a part of said measuring chirp signal emerging from said subject after interacting with tissue therein to be analyzed and forming an emerging signal propagating back along said first propagation path toward said semi-reflective mirror;

a fully-reflective mirror disposed a distance from said semi-reflective mirror in said second propagation path which directly and fully reflects said reference chirp signal back along said second propagation path toward said semi-reflective mirror so that said reference chirp signal has a defined phase relationship to said measuring chirp signal;

said fully-reflected reference chirp signal passing through said semi-reflective mirror and said emerging signal being deflected by said semi-reflective mirror so that both signals are superimposed forming an optical superposition signal having sets of beats, each set of beats having a respective beat frequency;

detector means, for receiving said optical superposition signal, for generating a corresponding electrical superposition signal;

filter means, supplied with said electrical superposition signal and having a transmission range with an upper limit frequency, for generating from said superposition signal a filtered signal having at least one beat frequency within said transmission range;

first adjustment means for adjusting the distance between said semi-reflective mirror and said fully reflective mirror;

second adjustment means for adjusting the distance between said semi-reflective mirror and said examination subject;

third adjustment means for adjusting the distance between said semi-reflective mirror and said detector means;

means for selecting said upper limit frequency of said filter means; and said first, second and third adjustment means and said means for adjusting said upper limit frequency forming, in combination, means for dimensioning the transit time of said measuring chirp signal outside said subject, the transit time of said reference chirp signal, and said upper limit frequency of said filter means for causing said filtered signal to represent substantially only parts of said emerging signal which have traversed an optical path length in said subject which does not exceed a defined maximum optical path length.

41. An apparatus for optically analyzing tissue in vivo comprising:

a coherent light source generating a coherent optical chirp signal of light selected from the group consisting of visible, NIR and IR light;

signal generator means for generating an electrical reference chirp signal supplied to said coherent light source for modulating said optical chirp signal so that said optical chirp signal has a defined phase relationship to said reference chirp signal;

a light exit zone, optically coupled to said coherent light source, from which the modulated optical chirp signal is directed, as a measuring chirp signal, at a tissue-containing subject, a part of said measuring chirp signal emerging from said subject after interacting with tissue therein to be analyzed and forming an optical emerging signal;

detector means, having a light entry zone into which said optical emerging signal enters, for converting said optical emerging signal into a corresponding electrical emerging signal;

mixer means for electronically mixing said electrical emerging signal with said reference chirp signal to form an electrical superposition signal having sets of beats, each set of beats having a respective beat frequency;

filter means, for receiving said electrical superposition signal and having a transmission range with an upper limit frequency, for generating from said superposition signal a filtered signal consisting of an electrical superposition signal having at least one beat frequency within said transmission range;

means for adjusting at least one of a distance between said signal generator means and said coherent light source, a distance between said signal generator means and said mixer means, a distance between said coherent light source and said light exit zone, a distance between said light entry zone and said mixer means, and said upper limit frequency for, in combination, dimensioning the transit time of said measuring chirp signal outside said subject, the transit time of said reference chirp signal and said upper limit frequency of said filter means for causing said filtered signal to represent substantially only parts of said optical emerging signal which have traversed an optical path length in said subject which does not exceed a defined maximum optical path length.

42. An apparatus as claimed in claim 41 further comprising means for disposing said light entry zone and said light exit zone in close proximity on a same side of said subject.

43. An apparatus as claimed in claim 42 further comprising means for generating relative motion between said light entry and exit zones, in combination, and said subject for scanning said subject.

44. An apparatus as claimed in claim 41 further comprising means for disposing said light exit zone and said light entry zone on opposite sides of said subject.

45. An apparatus as claimed in claim 44 further comprising means for generating relative motion between said light entry and exit zones, in combination, and said subject for scanning said subject.

46. An apparatus for optically analyzing tissue in vivo comprising:

a coherent light source generating a coherent optical chirp signal of light selected from the group consisting of visible, NIR and IR light;

signal generator means for generating an electrical reference chirp signal supplied to said coherent light source for modulating said coherent optical chirp signal;

a single light exit zone, optically coupled to said coherent light source, from which the modulated optical chirp signal, as a measuring chirp signal, exits toward a tissue-containing subject, a part of said measuring chirp signal emerging from said subject after interacting with tissue therein to be analyzed and forming an optical emerging signal;

a plurality of detector elements arranged around said subject at respective positions which are stationary relative to said subject;

means for generating relative motion between said light exit zone and said subject so that a part of said optical emerging signal is successively incident on said detector elements for scanning said subject, each detector element generating an electrical signal corresponding to the part of the optical emerging signal incident thereon;

a plurality of mixers corresponding in number to the plurality of detector elements, all of said mixers receiving said electrical reference chirp signal and said mixers respectively receiving said electrical signals from said detector elements, and each mixer superimposing the electrical signal from the detector element connected thereto with said electrical reference chirp signal to form a superposition signal having sets of beats, each set of beats having a respective beat frequency;

a plurality of filters corresponding in number to the plurality of mixers, said filters respectively receiving said superposition signals from said mixers, each filter having an identical upper limit frequency and generating from a superposition signal supplied thereto from a mixer a filtered signal having at least one beat frequency within said transmission range;

means for combining said filtered signals to form a combined filtered signal; and means for adjusting at least one of a distance between said signal generator means and said mixers, a distance between said coherent light source and said light exit zone and said upper limit frequency for, in combination, dimensioning the transit time of said measuring chirp signal outside said subject, the transit time of said electrical reference chirp signal, and said upper limit frequency of said filters for causing said combined filtered signal to represent substantially only parts of said optical emerging signal which have traversed an optical path length in said subject which does not exceed a defined maximum optical path length.

47. An apparatus for optically analyzing tissue in vivo comprising:

a coherent light source generating a coherent optical chirp signal of light selected from the group consisting of visible, NIR and IR light;

signal generator means for generating an electrical reference chirp signal supplied to said coherent light source for modulating said coherent optical chirp signal;

a plurality of light exit zones arranged around said subject at respective positions which are stationary relative to said subject, and means for successively, optically coupling said light exit zones one at a time to said coherent light source, from which the modulated optical chirp signal, as a measuring chirp signal, exits toward a tissue-containing subject, a part of said measuring chirp signal emerging from said subject after interacting with tissue therein to be analyzed and forming an optical emerging signal;

a plurality of detector elements arranged around said subject at respective positions which are stationary relative to said subject in alternation with said light exit zones, each detector element disposed to receive light from only one light exit zone;

each detector element generating an electrical signal corresponding to the part of the optical emerging signal incident thereon as said light zones are successively coupled to said coherent light source for scanning said subject;

a plurality of mixers corresponding in number to the plurality of detector elements, all of said mixers receiving said electrical reference chirp signal and said mixers respectively receiving said electrical signals from said detector elements, and each mixer superimposing the electrical signal from the detector element connected thereto with said electrical reference chirp signal to form a superposition signal having sets of beats, each set of beats having a respective beat frequency;

a plurality of filters corresponding in number to the plurality of mixers, said filters respectively receiving said superposition signals from said mixers, each filter having an identical upper limit frequency and generating from a electrical superposition signal received from a mixer a filtered signal having at least one beat frequency within said transmission range;

means for combining said filtered signals to form a combined filtered signal; and means for adjusting at least one of a distance between said signal generator means and said mixers, a distance between said coherent light source and said light exit zone and said upper limit frequency for, in combination, dimensioning the transit time of said measuring chirp signal outside said subject, the transit time of said electrical reference chirp signal, and said upper limit frequency of said filters for causing said combined filtered signal to represent substantially only parts of said optical emerging signal which have traversed an optical path length in said subject which does not exceed a defined maximum optical path length.

48. An apparatus for optically analyzing tissue in vivo comprising:

a plurality of coherent light sources each generating a coherent optical chirp signal of light selected from the group consisting of visible, NIR and IR light, said coherent light sources being arranged around a tissue-containing subject at respective positions which are stationary relative to said subject;

signal generator means for generating an electrical reference chirp signal supplied to said coherent light source for modulating said coherent optical chirp signal;

means for successively energizing said coherent light sources, one at a time for directing the modulated optical chirp signal, as a measuring chirp signal, at said containing subject for scanning said subject, a part of said measuring chirp signal emerging from said subject after interacting with tissue therein to be analyzed and forming an optical emerging signal;

a plurality of detector elements arranged around said subject at respective positions which are stationary relative to said subject, in alternation with said coherent light sources, each detector element disposed to receive light from only one of said coherent light sources so that a part of said optical emerging signal is successively incident on said detector elements as said coherent light sources are successively energized, each detector element generating an electrical signal corresponding to the part of the optical emerging signal incident thereon;

a plurality of mixers corresponding in number to the plurality of detector elements, all of said mixers receiving said electrical reference chirp signal and said mixers respectively receiving said electrical signals from said detector elements, and each mixer superimposing the electrical signal from the detector element connected thereto with said electrical reference chirp signal to form a superposition signal having sets of beats, each set of beats having a respective beat frequency;

a plurality of filters corresponding in number to the plurality of mixers, said filters respectively receiving said superposition signals from said mixers, each filter having an identical upper limit frequency and generating from an electrical superposition signal received from a mixer a filtered signal having at least one beat frequency within said transmission range;

means for combining said filtered signals to form a combined filtered signal; and means for adjusting at least one of a distance between said signal generator means and said mixers, a distance between said coherent light source and said light exit zone and said upper limit frequency for, in combination, dimensioning the transit time of said measuring chirp signal outside said subject, the transit time of said electrical reference chirp signal, and said upper limit frequency of said filters for causing said combined filtered signal to represent substantially only parts of said optical emerging signal which have traversed an optical path length in said subject which does not exceed a defined maximum optical path length.

49. A method for optically analyzing tissue in vivo comprising the steps of:
  directing a measuring chirp signal at a tissue-containing subject, said measuring chirp signal being a coherent optical signal of light selected from the group consisting of visible, NIR and IR light, a part of said measuring chirp signal emerging from said subject after interacting therein with tissue to be analyzed and forming an emerging signal;
  generating a reference chirp signal having a defined phase relationship to said measuring chirp signal;
  superimposing said emerging signal with said reference chirp signal to form a superposition signal having sets of beats, each set of beats having a respective beat frequency;
  filtering said superposition signal through a transmission range with an upper limit frequency, for generating from said superposition signal a filtered signal having at least one beat frequency within said transmission range; and
  dimensioning parameters including the transit time of said measuring chirp signal outside said subject, the transit time of said reference chirp signal, and said upper limit frequency of said filter means for causing said filtered signal to represent substantially only parts of said emerging signal which have traversed an optical path length in said subject which does not exceed a defined maximum optical path length.

50. A method as claimed in claim 49 wherein said transmission range also has a lower limit frequency, and wherein the step of dimensioning parameters includes dimensioning said lower limit frequency.

51. A method as claimed in claim 50 further comprising the step of: varying at least one of said parameters.

52. A method as claimed in claim 50 further comprising the steps of:
  calculating, from said filtered signal, said optical path length traversed in said subject by said part of said emerging signal represented in said filtered signal, based on said upper and lower limit frequencies of said filter means, said transit time of said measuring chirp signal outside said subject, and said transit time of said reference chirp signal.

53. A method as claimed in claim 49 or 50 comprising the additional step of calculating an at least two-dimensional absorption array of absorption coefficients of a region of said subject from said filtered signal.

54. A method as claimed in claim 53 comprising the additional step of graphically displaying the calculated absorption arrays with different chromatic values respectively allocated to different absorption coefficients.

55. A method as claimed in claim 53 comprising the additional step of graphically displaying the calculated absorption arrays with different grayscale values respectively allocated to different absorption coefficients.

56. A method as claimed in claim 49 wherein the steps of generating said measuring chirp signal and for generating said reference chirp signal are defined by generating said measuring chirp signal and said reference chirp signal in combination, from at least one coherent light source, and wherein said method comprises the additional steps of:
  generating a signal for frequency-modulating light from said coherent light source for causing said coherent light source to emit an optical chirp signal having an optical frequency varying in a defined manner over time;
  splitting said optical chirp signal into a first optical signal forming said measuring chirp signal and a second optical signal forming said reference chirp signal;
wherein the step of superimposing is further defined by optically superimposing said measuring chirp signal and said reference chirp signal to form an optical superposition signal, and wherein said method comprises the additional step of:
  opto-electronically detecting said optical superposition signal and converting it into an electrical signal which is filtered as said superposition signal.

57. A method as claimed in claim 49 wherein the steps of generating said measuring chirp signal and generating said reference chirp signal are further defined by generating said measuring chirp signal and said reference chirp signal, in combination, from at least one coherent light source, and wherein said method comprises the additional steps of:
  generating a signal for amplitude-modulating light from said coherent light source for causing said coherent light source to emit an optical chirp signal having an optical intensity changing over time at a frequency varying in a defined manner over time;
  splitting said optical chirp signal into a first optical signal forming said measuring chirp signal and a second optical signal forming said reference chirp signal;
wherein the step of superimposing is further defined by optically superimposing said measuring chirp signal and said reference chirp signal to form an optical superposition signal, and wherein said method comprises the additional step of:
  opto-electronically detecting said optical superposition signal and converting it into an electrical signal which is received by said filter means as said superposition signal.

58. A method as claimed in claim 56 or 57 wherein the step of splitting and superimposing are further defined, in combination, by directing said optical chirp signal onto a semi-reflective mirror at an angle deviating from 90° and thereby splitting said optical chirp signal into said measuring chirp signal and said reference chirp signal, propagating along different respective propagation paths, directly reflecting said reference chirp signal propagating away from said semi-reflective mirror back along said propagation path toward said semi-reflective mirror.

59. A method as claimed in claim 56 or 57 wherein the step of splitting is further defined by splitting said optical chirp signal in an optical fiber fan-out coupler and wherein the step of superimposing is further defined by superimposing said emerging signal and said reference chirp signal in an optical fiber fan-in coupler, and said method comprising the additional steps of:
  conducting said reference chirp signal from said optical fiber fan-out coupler to said optical fiber fan-in coupler in a first optical fiber;
  conducting said measuring chirp signal from said optical fiber fan-out coupler to said subject in a second optical fiber; and
  conducting said emerging signal to said optical fiber fan-in coupler in a third optical fiber.

60. An apparatus as claimed in claim 49 wherein the step of generating said measuring chirp signal is further defined by generating said measuring chirp signal from a coherent light source, wherein the step of generating said reference chirp signal is further defined by generating a first electrical signal forming said reference chirp signal and supplying said reference chirp signal to said coherent light source for causing said coherent light source to emit an amplitude-modulated signal, forming said measuring chirp signal, having an optical intensity changing over time at a frequency varying in a defined manner over time, and wherein said method comprises the additional step of:

opto-electronically converting said emerging signal into a second electrical signal, forming an electrical emerging signal, and wherein the step of superimposing is further defined by electronically mixing said reference chirp signal and said electrical emerging signal, for generating a third electrical signal, forming said superposition signal, which is filtered in the filtering step.

61. A method as claimed in claim 60 wherein the step of directing said measuring chirp signal at said subject is further defined by emitting said measuring chirp signal from a light exit zone from which said optical chirp signal exits toward said subject, and wherein said method comprises the additional steps of:

receiving said emerging signal via a light entry zone;
disposing said light exit zone and said light entry zone on opposite sides of said subject; and
generating relative movement between said light exit and light entry zones, in combination, and said subject for scanning said subject.

62. An apparatus as claimed in claim 60 wherein the step of directing said measuring chirp signal at said subject is further defined by emitting said measuring chirp signal from a light exit zone from which said optical chirp signal exits toward said subject, and wherein said method comprises the additional steps of:

receiving said emerging signal via a light entry zone;
disposing said light exit zone and said light entry zone being close proximity on the same side of said subject;
generating relative movement between said light exit and light entry zones, in combination, and said subject for scanning said subject.

63. A method as claimed in claim 60 wherein the step of directing said measuring chirp signal at said subject is further defined by emitting said measuring chirp signal from a light exit zone from which said optical chirp signal exits toward said subject, wherein the step of opto-electronically converting is further defined by respectively converting a part of said emerging signal into a plurality of electrical emerging signals in a plurality of separate detector elements, each detector element having a light entry zone into which said part of said emerging signal enters that detector element, and said method comprising the additional steps of:

generating a relative movement between said light exit zone and said subject for scanning said subject;
successively superimposing each of said plurality of electrical emerging signals with said reference chirp signal during said scanning.

64. A method as claimed in claim 60 wherein the step of directing said measuring chirp signal at said subject is further defined by emitting said measuring chirp signal from a plurality of light exit zones from which said optical chirp signal exits, one at a time, toward said examination subject for scanning said subject, and wherein said method comprises the additional steps of:

receiving said emerging signal in a plurality of separate detector elements corresponding in number to said plurality of light exit zones, each detector element having a light entry zone into which a part of said emerging signal enters that detector element, each light exit zone having one detector element, and thus one light entry zone, uniquely allocated thereto; and
successively directing said optical chirp signal out of each of said light exit zones for scanning said subject.

65. A method as claimed in claim 64 wherein the step of directing said measuring chirp signal at said subject is further defined by directing said optical chirp signal at said subject through a plurality of separate optical fibers, each optical fiber having a first end and having a second end forming one of said light exit zones, and wherein the step of successively directing said optical chirp signal out of each said light exit zone is further defined by moving a source of said coherent optical chirp signal through successive positions relative to said first ends for successively coupling said optical chirp signal into each of said first ends of said optical fibers for scanning said subject.

66. A method claimed in claim 60 wherein the step of directing said measuring chirp signal at said subject is further defined by emitting said measuring chirp signal from a light exit zone from which said optical chirp signal exits toward said subject, and wherein said method comprises the additional step of:

disposing said light exit zone and said light entry zone on opposite sides of said subject; and
generating relative movement between said light exit and light entry zones, in combination, and said subject for scanning said subject.

67. A method for optically analyzing tissue in vivo comprising the steps of:

generating a coherent optical chirp signal of light selected from the group consisting of visible, NIR and IR light;
splitting said optical chirp signal, at a splitting location, into a measuring chirp signal and a reference chirp signal having a defined phase relationship to said measuring chirp signal;
selecting one fiber from a first group of optical fibers, having respectively different combinations of refractive index and length, to conduct said measuring chirp signal from said splitting location to a tissue-containing subject, a part of said measuring chirp signal emerging from said subject after interacting with tissue therein to be analyzed and forming an emerging signal;
superimposing said emerging signal, at a superimposing location, with said reference chirp signal to form an optical superposition signal having sets of beats, each set of beats having a respective beat frequency;
selecting one fiber from a second group of separate optical fibers, having respectively different combinations of refractive index and length, for conducting said reference chirp signal from said splitting location to said superimposing location;
selecting one fiber from a third group of separate optical fibers, having respectively different combinations of refractive index and length, for conducting said emerging signal from said subject to said superimposing location;
converting said optical superposition signal into an electrical superposition signal;
filtering said electrical superposition signal through a transmission range with an upper limit frequency, for generating from said electrical superposition signal a filtered signal having at least one beat frequency within said transmission range; and selecting said upper limit frequency, in combination with the transit time of said measuring chirp signal outside said subject defined by selecting respective ones of said optical fibers in said first and third groups and the transit time of said reference chirp signal defined by selecting one of said optical fibers in said second group, for causing said filtered signal to represent substantially only parts of said emerging signal which have traversed an optical path length in said subject which does not exceed a defined maximum optical path length.

68. A method as claimed in claim 67 wherein the selected one of said optical fibers in said first group has an end facing said subject forming a light exit zone from which said measuring chirp signal exits toward said subject and wherein the selected one of said optical fibers in said third group has an end facing said subject forming a light entry zone into which said emerging signal enters, and wherein said method comprises the additional step of disposing said light entry zone and said light exit zone in close proximity on a same side of said subject.

69. A method as claimed in claim 67 wherein the selected one of said optical fibers in said first group has an end facing said subject forming a light exit zone from which said measuring chirp signal exits toward said subject and wherein the selected one of said optical fibers in said third group has an end facing said subject forming a light entry zone into which said emerging signal enters, and wherein said method comprises the additional step of disposing said light entry zone and said light exit zone on opposite sides of said subject.

70. A method as claimed in claim 67 wherein the selected one of said optical fibers in said first group has an end facing said subject forming a light exit zone from which said measuring chirp signal exits toward said subject and wherein the selected one of said optical fibers in said third group has an end facing said subject forming a light entry zone into which said emerging signal enters, and wherein said method comprises the additional steps of disposing said light entry zone and said light exit zone in close proximity on a same side of said subject; and generating relative motion between said light entry and exit zones, in combination, and said subject for scanning said subject.

71. A method as claimed in claim 67 wherein the selected one of said optical fibers in said first group has an end facing said subject forming a light exit zone from which said measuring chirp signal exits toward said subject and wherein the selected one of said optical fibers in said third group has an end facing said subject forming a light entry zone into which said emerging signal enters, and wherein said method comprises the additional steps of disposing said light entry zone and said light exit zone on opposite sides of said subject; and generating relative motion between said light entry and exit zones, in combination, and said subject for scanning said subject.

72. A method for optically analyzing tissue in vivo comprising the steps of:

generating a coherent optical chirp signal of light selected from the group consisting of visible, NIR and IR light, said optical chirp signal propagating along a first propagation path;

directing said optical chirp signal at a semi-reflective mirror disposed in said first propagation path at an angle deviating from 90° for splitting said optical chirp signal into a measuring chirp signal which continues to propagate along said first propagation path toward a tissue-containing subject, and a reference chirp signal propagating along a second propagation path, different from said first propagation path, a part of said measuring chirp signal emerging from said subject after interacting with tissue therein to be analyzed and forming an emerging signal propagating back along said first propagation path toward said semi-reflective mirror;

disposing a fully-reflective mirror a distance from said semi-reflective mirror in said second propagation path for directly and fully reflecting said reference chirp signal back along said second propagation path toward said semi-reflective mirror so that said reference chirp signal has a defined phase relationship to said measuring chirp signal;

passing said fully reflected reference chirp signal through said semi-reflective mirror and deflecting said emerging signal by said semi-reflective mirror for superimposing both signals to form an optical superposition signal having sets of beats, each set of beats having a respective beat frequency;

converting said optical superposition signal, at a converting location into a corresponding electrical superposition signal;

filtering said electrical superposition signal through a transmission range with an upper limit frequency, for generating from said electrical superposition signal a filtered signal having at least one beat frequency within said transmission range;

adjusting the distance between said semi-reflective mirror and said fully reflective mirror;

adjusting the distance between said semi-reflective mirror and said examination subject;

adjusting the distance between said semi-reflective mirror and said converting location;

selecting said upper limit frequency; and selectively adjusting said distances and said upper limit frequency, in combination, for dimensioning the transit time of said measuring chirp signal outside said subject, the transit time of said reference chirp signal, and said upper limit frequency for causing said filtered signal to represent substantially only parts of said emerging signal which have traversed an optical path length in said subject which does not exceed a defined maximum optical path length.

73. A method for optically analyzing tissue in vivo comprising the steps of:

generating a coherent optical chirp signal from a coherent light source emitting light selected from the group consisting of visible, NIR and IR light;

generating, from a generator source, an electrical reference chirp signal supplied to said coherent light source for modulating said optical chirp signal so that said optical chirp signal has a defined phase relationship to said reference chirp signal;

optically coupling a light exit zone, to said coherent light source, from which the modulated optical chirp signal is directed, as a measuring chirp signal, at a tissue-containing subject, a part of said measuring chirp signal emerging from said subject after interacting with tissue therein to be analyzed and forming an optical emerging signal;

receiving said optical emerging signal via a light entry zone and converting said optical emerging signal into a corresponding electrical emerging signal;

electronically mixing said electrical emerging signal, at a mixing location, with said reference chirp signal to form an electrical superposition signal having sets of beats, each set of beats having a respective beat frequency;

filtering said electrical superposition signal through a transmission range with an upper limit frequency, for generating from said electrical superposition signal a filtered signal having at least one beat frequency within said transmission range;

adjusting at least one of a distance between said generator source means and said coherent light source, a distance between said signal generator source and said mixing location, a distance between said coherent light source and said light exit zone, a distance between said light entry zone and said mixing location, and said upper limit frequency for, in combination, dimensioning the transit time of said measuring chirp signal outside said subject, the transit time of said reference chirp signal and said upper limit frequency of said filter means for causing said filtered signal to represent substantially only parts of said optical emerging signal which have traversed an optical path length in said subject which does not exceed a defined maximum optical path length.

74. A method as claimed in claim 73 comprising the additional step of disposing said light entry zone and said light exit zone in close proximity on a same side of said subject.

75. A method as claimed in claim 74 comprising the additional step of generating relative motion between said light entry and exit zones, in combination, and said subject for scanning said subject.

76. A method as claimed in claim 74 comprising the additional step of disposing said light exit zone and said light entry zone on opposite sides of said subject.

77. A method as claimed in claim 76 comprising the additional step of generating relative motion between said light entry and exit zones, in combination, and said subject for scanning said subject.

78. A method for optically analyzing tissue in vivo comprising the steps of:
generating a coherent optical chirp signal from a coherent light source emitting light selected from the group consisting of visible, NIR and IR light;
generating, from a generator source, an electrical reference chirp signal supplied to said coherent light source for modulating said coherent optical chirp signal;
optically coupling a single light exit zone, to said coherent light source, from which the modulated optical chirp signal, as a measuring chirp signal, is directed at a tissue-containing subject, a part of said measuring chirp signal emerging from said subject after interacting with tissue therein to be analyzed and forming an optical emerging signal;
arranging a plurality of detector elements around said subject at respective positions which are stationary relative to said subject;
generating relative motion between said light exit zone and said subject so that a part of said optical emerging signal is successively incident on said detector elements for scanning said subject, each detector element generating an electrical signal corresponding to the part of the optical emerging signal incident thereon;

superimposing each of the respective electrical signals from the detector elements at a mixing location with said electrical reference chirp signal to form a plurality of superposition signals each having sets of beats, each set of beats having a respective beat frequency;

separately fitting each of said superposition signals through transmission ranges identical upper limit frequency and thereby generating from said electrical superposition signals a plurality of respective filtered signals each having at least one beat frequency within said transmission range;

combining said filtered signals to form a combined filtered signal; and adjusting at least one of a distance between said generator source and said mixing location, a distance between said coherent light source and said light exit zone and said upper limit frequency for, in combination, dimensioning the transit time of said measuring chirp signal outside said subject, the transit time of said electrical reference chirp signal, and said upper limit frequency for causing said combined filtered signal to represent substantially only parts of said optical emerging signal which have traversed an optical path length in said subject which does not exceed a defined maximum optical path length.

79. A method for optically analyzing tissue in vivo comprising the steps of:
generating a coherent optical chirp signal from a coherent light source emitting light selected from the group consisting of visible, NIR and IR light;
generating, from a generator source an electrical reference chirp signal supplied to said coherent light source for modulating said coherent optical chirp signal;
arranging a plurality of light exit zones around said subject at respective positions which are stationary relative to said subject, and for successively, optically coupling said light exit zones one at a time to said coherent light source, from which the modulated optical chirp signal, as a measuring chirp signal, exits toward a tissue-containing subject, a part of said measuring chirp signal emerging from said subject after interacting with tissue therein to be analyzed and forming an optical emerging signal;
arranging a plurality of detector elements arranged around said subject at respective positions which are stationary relative to said subject in alternation with said light exit zones, each detector element disposed to receive light from only one light exit zone;
generating from each detector element an electrical signal corresponding to the part of the optical emerging signal incident thereon as said light zones are successively coupled to said coherent light source for scanning said subject for scanning said subject;
superimposing each electrical signal from each detector element at a mixing location with said electrical reference chirp signal to form a plurality of superposition signals having sets of beats, each set of beats having a respective beat frequency;

separately filtering said superposition signals through transmission ranges having an identical upper limit frequency and thereby generating from said electrical superposition signals supplied thereto from a mixer a plurality of respective filtered signals each having at lease one beat frequency within said transmission range;

combining said filtered signals to form a combined filtered signal; and adjusting at least one of a distance between said generator source and said mixing location, a distance between said coherent light source and said light exit zone and said upper limit frequency for, in combination, dimensioning the transit time of said measuring chirp signal outside said subject, the transit time of said electrical reference chirp signal, and said upper limit frequency for causing said combined filtered signal to represent substantially only parts of said optical emerging signal which have traversed an optical path length in said subject which does not exceed a defined maximum optical path length.

80. A method for optically analyzing tissue in vivo comprising the steps of:

generating a plurality of coherent optical chirp signals from a plurality of coherent light sources each emitting light selected from the group consisting of visible, NIR and IR light;

arranging said coherent light sources being arranged around a tissue-containing subject at respective positions which are stationary relative to said subject;

generating, from a generator source, an electrical reference chirp signal supplied to said coherent light source for modulating said coherent optical chirp signal;

successively energizing said coherent light sources, one at a time for directing the modulated optical chirp signal, as a measuring chirp signal, at said containing subject for scanning said subject, a part of said measuring chirp signal emerging from said subject after interacting with tissue therein to be analyzed and forming an optical emerging signal;

arranging a plurality of detector elements around said subject at respective positions which are stationary relative to said subject, in alternation with said coherent light sources, each detector element disposed to receive light from only one of said coherent light sources so that a part of said optical emerging signal is successively incident on said detector elements as said coherent light sources are successively energized, and generating from each detector element an electrical signal corresponding to the part of the optical emerging signal incident thereon;

superimposing each electrical signal from each detector element at a mixing location with said electrical reference chirp signal to form a plurality of superposition signals each having sets of beats, each set of beats having a respective beat frequency;

separately filtering said superposition signals through transmission ranges having an identical upper limit frequency and thereby generating from said superposition signals a plurality of respective filtered signals each having at least one beat frequency within said transmission range;

combining said filtered signals to form a combined filtered signal; and adjusting at least one of a distance between said generator source and said mixing location, a distance between said coherent light source and said light exit zone and said upper limit frequency for, in combination, dimensioning the transit time of said measuring chirp signal outside said subject, the transit time of said electrical reference chirp signal, and said upper limit frequency for causing said combined filtered signal to represent substantially only parts of said optical emerging signal which have traversed an optical path length in said subject which does not exceed a defined maximum optical path length.

* * * * *